United States Patent
Wood et al.

(10) Patent No.: US 10,376,472 B2
(45) Date of Patent: *Aug. 13, 2019

(54) ELECTROSTATIC PRINTING OF CYCLODEXTRIN COMPOSITIONS

(71) Applicant: Cellresin Technologies, LLC, Bloomington, MN (US)

(72) Inventors: Willard E. Wood, Arden Hills, MN (US); Joseph S. Keute, Blaine, MN (US)

(73) Assignee: Cellresin Technologies, LLC, Bloomington, MN (US)

(*) Notice: Subject to any disclaimer, the term of this patent is extended or adjusted under 35 U.S.C. 154(b) by 304 days.

This patent is subject to a terminal disclaimer.

(21) Appl. No.: 15/208,040

(22) Filed: Jul. 12, 2016

(65) Prior Publication Data

US 2016/0317461 A1  Nov. 3, 2016

Related U.S. Application Data

(63) Continuation of application No. 14/748,456, filed on Jun. 24, 2015, now Pat. No. 9,421,793.

(60) Provisional application No. 62/017,492, filed on Jun. 26, 2014.

(51) Int. Cl.

| | | |
|---|---|---|
| A61K 47/69 | (2017.01) | |
| A61K 9/70 | (2006.01) | |
| B32B 3/10 | (2006.01) | |
| B05D 1/18 | (2006.01) | |
| B41J 2/41 | (2006.01) | |
| G03G 9/087 | (2006.01) | |
| G03G 9/093 | (2006.01) | |
| G03G 9/097 | (2006.01) | |
| A61K 9/00 | (2006.01) | |
| A61K 47/40 | (2006.01) | |

(52) U.S. Cl.
CPC .............. *A61K 9/703* (2013.01); *A61K 9/006* (2013.01); *A61K 9/0014* (2013.01); *A61K 47/40* (2013.01); *A61K 47/6951* (2017.08); *B05D 1/18* (2013.01); *B32B 3/10* (2013.01); *B41J 2/41* (2013.01); *G03G 9/08775* (2013.01); *G03G 9/08777* (2013.01); *G03G 9/09335* (2013.01); *G03G 9/09758* (2013.01); *G03G 9/09775* (2013.01); *Y10T 428/24802* (2015.01)

(58) Field of Classification Search
CPC ........................... Y10T 428/24802; B41J 2/41; A61K 47/6951
See application file for complete search history.

(56) References Cited

U.S. PATENT DOCUMENTS

| | | |
|---|---|---|
| 3,493,362 A | 2/1970 | Ferm |
| 3,661,549 A | 5/1972 | Freytag et al. |
| 3,676,102 A | 7/1972 | Clark et al. |
| 3,810,749 A | 5/1974 | Young |
| 3,840,448 A | 10/1974 | Osborn et al. |
| 3,879,188 A | 4/1975 | Fritz et al. |
| 3,885,950 A | 5/1975 | Ehrig et al. |
| 3,940,667 A | 2/1976 | Pearce |
| 3,943,103 A | 3/1976 | Borden et al. |
| 4,162,165 A | 7/1979 | Schwab |
| 4,181,752 A | 1/1980 | Martens et al. |
| 4,356,115 A | 10/1982 | Shibanai et al. |
| 4,432,802 A | 2/1984 | Harata et al. |
| 4,438,106 A | 3/1984 | Wagu et al. |
| 4,547,572 A | 10/1985 | Fenyvesi et al. |
| 4,575,548 A | 3/1986 | Ueda et al. |
| 4,636,343 A | 1/1987 | Shibanai |
| 4,675,395 A | 6/1987 | Fukazawa et al. |
| 4,677,177 A | 6/1987 | Shibanai et al. |
| 4,681,934 A | 7/1987 | Shibanai et al. |
| 4,711,936 A | 12/1987 | Shibanai et al. |
| 4,722,815 A | 2/1988 | Shibanai |
| 4,725,633 A | 2/1988 | Shibanai |
| 4,725,657 A | 2/1988 | Shibanai |
| 4,728,510 A | 3/1988 | Shibanai et al. |
| 4,732,758 A | 3/1988 | Hurion et al. |
| 4,732,759 A | 3/1988 | Shibanai et al. |
| 4,769,242 A | 9/1988 | Shibanai |
| 4,772,291 A | 9/1988 | Shibanai et al. |

(Continued)

FOREIGN PATENT DOCUMENTS

| | | |
|---|---|---|
| AU | 2011268471 B1 | 3/2012 |
| CA | 2011748 A1 | 9/1991 |

(Continued)

OTHER PUBLICATIONS

Machine translation of detailed description of JP 2002-174925 acquired Aug. 5, 2018.*
Examination Report (Communication pursuant to Article 94(3) EPC) for European Application No. 15735823.5, dated Mar. 5, 2018, 7 pages.
Office Action for Israeli Application No. 244176, dated Jun. 6, 2017, 2 pages of English Translation.
Office Action for Israeli Application No. 244176, dated Nov. 22, 2016, 4 pages of English Translation.

(Continued)

*Primary Examiner* — Gerard Higgins
(74) *Attorney, Agent, or Firm* — Kagan Binder, PLLC

(57) ABSTRACT

Disclosed herein are methods of electrostatically printing a cyclodextrin composition on a substrate, the method including forming an electrostatically printable composition comprising a polymer and one or more cyclodextrins, one or more cyclodextrin inclusion complexes, or a combination thereof, and electrostatically printing the composition on a substrate. Also described are electrostatically printable compositions, methods of making the compositions, printing systems employing the compositions, substrates having the composition electrostatically printed thereon, laminates thereof, and uses of the printed substrates and laminates.

19 Claims, 1 Drawing Sheet

(56) References Cited

U.S. PATENT DOCUMENTS

| | | |
|---|---|---|
| 4,833,674 A | 5/1989 | Takai et al. |
| 4,834,985 A | 5/1989 | Elger et al. |
| 4,847,151 A | 7/1989 | Ichiro |
| 4,871,541 A | 10/1989 | Shibanai |
| 4,883,674 A | 11/1989 | Fan |
| 5,070,081 A | 12/1991 | Majid et al. |
| 5,078,920 A | 1/1992 | Maza |
| 5,100,462 A | 3/1992 | Sisler et al. |
| 5,183,655 A | 2/1993 | Stanislowski et al. |
| 5,360,899 A | 11/1994 | Nussstein et al. |
| 5,474,698 A | 12/1995 | Rolando et al. |
| 5,505,969 A | 4/1996 | Wood et al. |
| 5,518,988 A | 5/1996 | Sisler et al. |
| 5,627,002 A | 5/1997 | Pan et al. |
| 5,656,369 A * | 8/1997 | Chess ............... B42D 5/027 428/331 |
| 5,723,714 A | 3/1998 | Binger |
| 5,730,311 A | 3/1998 | Curtis |
| 5,760,129 A | 6/1998 | Lau |
| 5,776,842 A | 7/1998 | Wood et al. |
| 5,789,123 A | 8/1998 | Cleckner et al. |
| 5,827,627 A | 10/1998 | Cleckner et al. |
| 5,832,699 A | 11/1998 | Zobel |
| 5,985,772 A | 11/1999 | Wood et al. |
| 6,017,849 A | 1/2000 | Daly et al. |
| 6,092,761 A | 7/2000 | Mushaben |
| 6,162,533 A | 12/2000 | Onozawa et al. |
| 6,194,350 B1 | 2/2001 | Sisler |
| 6,206,947 B1 | 3/2001 | Evans et al. |
| 6,218,013 B1 | 4/2001 | Wood et al. |
| 6,232,365 B1 | 5/2001 | Weiss et al. |
| 6,271,127 B1 | 8/2001 | Liu et al. |
| 6,296,923 B1 | 10/2001 | Zobel |
| 6,313,068 B1 | 11/2001 | Daly et al. |
| 6,358,670 B1 | 3/2002 | Wong et al. |
| 6,365,549 B2 | 4/2002 | Sisler |
| 6,426,319 B1 | 7/2002 | Kostansek |
| 6,444,619 B1 | 9/2002 | Kostansek |
| 6,451,065 B2 | 9/2002 | Trinh et al. |
| 6,452,060 B2 | 9/2002 | Jacobson |
| 6,548,132 B1 | 4/2003 | Clarke et al. |
| 6,548,448 B2 | 4/2003 | Kostansek |
| 6,613,703 B1 | 9/2003 | Yahiaoui et al. |
| 6,709,746 B2 | 3/2004 | Wood et al. |
| 6,720,476 B2 | 4/2004 | Clendennen et al. |
| 6,739,110 B2 | 5/2004 | Ogden et al. |
| 6,762,153 B2 | 7/2004 | Kostansek et al. |
| 6,766,612 B1 | 7/2004 | Liu |
| 6,770,600 B1 | 8/2004 | Lamola et al. |
| 6,831,116 B2 | 12/2004 | Bitler et al. |
| 6,852,904 B2 | 2/2005 | Sun et al. |
| 6,953,540 B2 | 10/2005 | Chong et al. |
| 6,987,099 B2 | 1/2006 | Trinh et al. |
| 7,001,661 B2 | 2/2006 | Beaverson et al. |
| 7,019,073 B2 | 3/2006 | Etherton et al. |
| 7,041,625 B2 | 5/2006 | Jacobson et al. |
| 7,157,411 B2 | 1/2007 | Rohde et al. |
| 7,166,671 B2 | 1/2007 | Wood et al. |
| 7,169,451 B2 | 1/2007 | Clarke et al. |
| 7,182,941 B2 | 2/2007 | Trinh et al. |
| 7,365,123 B2 | 4/2008 | Wood et al. |
| 7,531,471 B2 | 5/2009 | Quincy, III |
| 7,547,443 B2 | 6/2009 | Krzysik et al. |
| 7,549,396 B2 | 6/2009 | Hurwitz et al. |
| 7,569,160 B2 | 8/2009 | Oldenzijl et al. |
| 7,601,374 B2 | 10/2009 | Clarke |
| 7,629,042 B2 | 12/2009 | Jones et al. |
| 7,637,054 B2 | 12/2009 | Alfrey et al. |
| 7,713,561 B2 | 5/2010 | Popa et al. |
| 7,758,885 B2 | 7/2010 | Myhra |
| 7,799,885 B2 | 9/2010 | Shustack et al. |
| 7,943,549 B2 | 5/2011 | Pierce et al. |
| 7,997,026 B2 | 8/2011 | Webster et al. |
| 8,093,430 B2 | 1/2012 | Sisler |
| 8,168,860 B2 | 5/2012 | Rosichan et al. |
| 8,247,459 B2 | 8/2012 | Kostansek |
| 8,314,051 B2 | 11/2012 | Yoo |
| 8,414,989 B2 | 4/2013 | Wood et al. |
| 8,461,086 B2 | 6/2013 | Chang et al. |
| 8,481,127 B2 | 7/2013 | Wood et al. |
| 8,603,524 B2 | 12/2013 | Baier et al. |
| 9,320,288 B2 | 4/2016 | Wood et al. |
| 2002/0007055 A1 | 1/2002 | Uchiyama et al. |
| 2002/0012759 A1 | 1/2002 | Asayama et al. |
| 2002/0058592 A1 | 5/2002 | Kostansek |
| 2002/0150829 A1 | 10/2002 | Zhao et al. |
| 2002/0164444 A1 | 11/2002 | Hunt et al. |
| 2002/0198107 A1 | 12/2002 | Kostansek |
| 2003/0022082 A1 | 1/2003 | Ohmura et al. |
| 2003/0170570 A1 | 9/2003 | Vander Aa et al. |
| 2003/0186032 A1* | 10/2003 | Rosenberger ............ G03G 8/00 428/195.1 |
| 2005/0043482 A1 | 2/2005 | Etherton et al. |
| 2005/0069804 A1 | 3/2005 | Qian et al. |
| 2005/0260907 A1 | 11/2005 | Chang et al. |
| 2005/0261131 A1 | 11/2005 | Basel et al. |
| 2005/0261426 A1 | 11/2005 | Wood et al. |
| 2006/0020069 A1 | 1/2006 | Michel et al. |
| 2006/0164822 A1 | 7/2006 | Kobayashi et al. |
| 2007/0003741 A1 | 1/2007 | Sakurai et al. |
| 2007/0105722 A1 | 5/2007 | Basel et al. |
| 2009/0088323 A1 | 4/2009 | Basel et al. |
| 2009/0220739 A1 | 9/2009 | Chougule |
| 2009/0245876 A1 | 10/2009 | Tohata et al. |
| 2010/0144533 A1 | 6/2010 | Baier et al. |
| 2011/0033540 A1 | 2/2011 | Daniloff et al. |
| 2011/0143004 A1 | 6/2011 | Wood et al. |
| 2011/0253562 A1 | 10/2011 | Machado |
| 2012/0004108 A1 | 1/2012 | Zhen |
| 2012/0107459 A1 | 5/2012 | Wood et al. |
| 2012/0258220 A1 | 10/2012 | Jacobson |
| 2013/0029058 A1 | 1/2013 | Wood et al. |
| 2013/0223886 A1 | 8/2013 | Miyagawa et al. |
| 2014/0011679 A1 | 1/2014 | Mir |
| 2015/0196022 A1 | 7/2015 | Jensen et al. |

FOREIGN PATENT DOCUMENTS

| | | |
|---|---|---|
| CA | 2692211 A1 | 8/2010 |
| CN | 1371603 A | 10/2002 |
| CN | 1457636 A | 11/2003 |
| CN | 1619427 A | 5/2005 |
| CN | 1675595 A | 9/2005 |
| CN | 1703955 A | 12/2005 |
| CN | 101104665 A | 1/2008 |
| CN | 101297659 A | 11/2008 |
| CN | 201501603 U | 6/2010 |
| CN | 101990937 A | 3/2011 |
| CN | 102047946 A | 5/2011 |
| CN | 102119719 A | 7/2011 |
| CN | 102532611 A | 7/2012 |
| DE | 4035378 A1 | 5/1992 |
| EP | 0180468 A2 | 5/1986 |
| EP | 0514578 A1 | 11/1992 |
| EP | 1236397 A2 | 9/2002 |
| EP | 1559746 A1 | 8/2005 |
| EP | 1593306 A2 | 11/2005 |
| EP | 2383614 A2 | 11/2011 |
| EP | 2389814 A1 | 11/2011 |
| EP | 2508071 A1 | 10/2012 |
| GB | 1119545 A | 7/1968 |
| GB | 2492284 A | 12/2012 |
| GB | 2491424 B | 4/2013 |
| JP | H06118719 A | 4/1994 |
| JP | 8-100027 A | 4/1996 |
| JP | 2002174925 A | 6/2002 |
| JP | 2002281894 A | 10/2002 |
| JP | 2002-356401 A | 12/2002 |
| JP | 2005258333 A | 9/2005 |
| JP | 2007-137882 A | 6/2007 |
| JP | 2007-256773 A | 10/2007 |
| JP | 2008-052021 A | 3/2008 |
| JP | 2009-029970 A | 2/2009 |
| JP | 2012-122079 A | 6/2012 |

(56) References Cited

FOREIGN PATENT DOCUMENTS

| | | |
|---|---|---|
| JP | 2013-510887 A | 3/2013 |
| JP | 2013-254123 A | 12/2013 |
| NZ | 514235 | 7/2002 |
| NZ | 514236 | 1/2003 |
| NZ | 521818 | 3/2004 |
| NZ | 524289 | 7/2004 |
| NZ | 539684 | 12/2006 |
| NZ | 551211 | 12/2008 |
| NZ | 554976 | 3/2009 |
| NZ | 563094 | 4/2009 |
| NZ | 568774 | 12/2009 |
| NZ | 578429 | 12/2011 |
| TW | 201311803 A | 3/2013 |
| WO | WO8605798 A1 | 10/1986 |
| WO | WO0113968 A1 | 3/2001 |
| WO | WO 02/20668 A2 | 3/2002 |
| WO | WO2006046254 A1 | 5/2006 |
| WO | WO2006072180 A1 | 7/2006 |
| WO | WO2008089140 A1 | 7/2008 |
| WO | WO2011081877 A1 | 7/2011 |
| WO | WO2011109144 A1 | 9/2011 |
| WO | WO2012134539 A1 | 10/2012 |
| WO | WO2014085518 A1 | 6/2014 |

OTHER PUBLICATIONS

Office Action for Japanese Patent Application No. 2016-516058, dated Aug. 3, 2016, 11 pages (7 pages of English Translation and 4 pages Official Copy).
Office Action for Colombian Patent Application No. NC2017/0000408, dated Jan. 25, 2017, 4 pages (2 pages English Translation and 2 pages Official Copy).
First Examination Report dated May 12, 2015 in connection with Australian Patent Application No. 2014203711.
English Translation of Official Communication dated Jul. 9, 2015 in connection with Israeli Patent Application No. 228558.
Parafilm® M, Brand, "Seals tightly, quickly and universally: Parafilm® M Sealing Film." GmbH + Co., Wertheim, Germany, 4 pages.
Schotsmans et al. "Methylcyclopropene: Mode of action and relevance in postharvest horticulture research", Horticultural Reviews, vol. 35, Purdue University. 2009. Chatper 5, pp. 263-313.
Blankenship, Sylvia. "Ethylene: The Ripening Hormone", Postharvest Information Network, WSU Tree Fruit Research & Extension Center, obtained Nov. 28, 2012 from <http://postharvest.tfrec.wsu.edu/pages/PC2000F>, 2 pages.
Non-Final Office Action dated Apr. 9, 2015 in U.S. Appl. No. 14/619,905, 9 pages.
First Examination Report dated Apr. 2, 2014 in Australian Application No. 2013302242.
"Petrolatum," Pharmaceutical Excipients, London, Pharmaceutical Press, Electronic Version, 2006 <http://www.medicinescomplete.com/mc/excipients/current/1000304196.htm> 5 pages.
Office Action dated Nov. 27, 2014 in Canadian Application No. 2,867,732.
Fatty Acid Melting Points <http://www.chemicalland21.com/lifescience/foco/BEHENIC%20ACID.htm> Nov. 21, 2013.
Office Action dated Aug. 3, 2015 in Chinese Application No. 201410461847.X, with English translation. 13 pages.
Official Notification dated Aug. 13, 2015 in Israeli Patent Application No. 228558, 2 pages.
Examination Report dated Sep. 2, 2015 in Australian Application No. 2014227446, 4 pages.
The International Search Report and Written Opinion dated Sep. 4, 2015 in International Application No. PCT/US2015/037707.
Examination Report dated Aug. 12, 2015 in Australian Patent Application No. 2015203550.
Examination Report dated Sep. 22, 2015 in Australian Patent Application No. 2015203550.
Office Action dated Nov. 2, 2010 in Canadian Patent Application No. 2,692,211 (2 pages).
Office Action dated Feb. 9, 2011 in Canadian Patent Application No. 2,692,211 (1 page).
International Preliminary Report on Patentability dated Apr. 28, 2011 in International Application No. PCT/US2010/060067.
Combined Search and Examination Report dated Jan. 13, 2012 in United Kingdom Application No. GB1119545.0.
International Search Report and Written Opinion dated Jan. 30, 2012 in International Application No. PCT/US2011/057017.
Examination Report dated Feb. 6, 2012 in Australian Application No. AU2011268471.
Examination Report dated Apr. 4, 2012 in United Kingdom Application No. GB1119545.0.
Non-Final Office Action dated Apr. 27, 2012 in U.S. Appl. No. 13/287,944.
International Preliminary Report on Patentability dated Jun. 28, 2012 in International Application No. PCT/US2010/060067.
Examination Report dated Sep. 11, 2012 in United Kingdom Application No. GB1119545.0.
Combined Search and Examination Report dated Oct. 23, 2012 in United Kingdom Application No. GB1218077.4.
Final Office Action dated Nov. 8, 2012 in U.S. Appl. No. 13/287,944.
Examination Report dated Nov. 9, 2012 in Australian Application No. AU2010337146.
Non-Final Office Action dated Nov. 26, 2012 in U.S. Appl. No. 12/967,226.
Notice of Allowance dated Feb. 8, 2013 in U.S. Appl. No. 13/287,944.
Examination Report dated Feb. 19, 2013 in Australian Application No. AU2010337146.
Examination Report dated Mar. 22, 2013 in Australian Application No. AU2012203412.
Final Office Action dated Apr. 26, 2013 in U.S. Appl. No. 12/967,226.
"AFFINITYTM kc 8852G, Polyolefin Plastomer," Form No. 400-00050072en, REv: Jun. 3, 2009, The Dow Chemical Company, www.dowplastics.com (2009).
"AFFINITYTM PF 1140G, Polyolefin Plastomer," Form No. 400-00071417en, Rev: Jun. 3, 2009, The Dow Chemical Company, www.dowplastics.com (2009).
Ambaw, Alemayehu et al. "Modeling of Diffusion-Adsorption Kinetics of 1-Methylcyclopropene (1-MCP) in Apple Fruit and Non-Target Materials in Storage Rooms," (2010) 5 pgs.
Amiel, Catherine. "Cyclodextrin polymers and drug delivery," Systemes Polymeres Complexes, ICMPE J. Drug Del. Sci. Tech. (2004) 21 pgs.
"Basell—Polybutene-1 PB 0300M-Polybutene-1," http://basell.com/portal/binary/com.vignette.vps.basell.productgrade.ProductGradeFileDisplay?id27d684b40c337010VgnVC . . . (Jul. 18, 2006) 2 pgs.
Blankenship, Sylvia M. et al. "1-Methylcyclopropene: a review," Postharvest Biology and Technology, 28 (2003) 25 pgs.
Burg, Stanley P. et al. "Molecular Requirements for the Biological Activity of Ethylene," Plant Physiolo. 42, pp. 144-152 (1967).
Chanda, Manas et al. "Plastics Technology Handbook," 4th Ed., CRC Press, p. 1-34 (1 page).
Cheng, Jianjun et al. "Synthesis of Linear, B-Cyclodextrin-Based Polymers and Their Camptothecin Conjugates," Bioconjugate Chem. 14 (2003) pp. 1007-1017.
DeEll, Jennifer R. et al. "1-Methylcyclopropene Influences 'Empire' and 'Delicious' Apple Quality during Long-term Commercial Storage," HortTechnology, Jan.-Mar. 2007, 17(1) pp. 46-51.
Denter, U. et al. "Surface modification of synthetic and natural fibres by fixation of cyclodextrin derivatives," Journal of Inclusion Phenomena an dMolecular Recognition in Chemistry 25, pp. 197-202, 1996.
"DuPontTM FusabondR P MD353D," DuPont Packaging & Industrial Polymers, http://www.dupont.com (Jun. 2005) 2 pgs.
"Conclusion regarding the peer review of the pesticide risk assessment of the active substance 1-methylcyclopropene," EFSA Scientific Report (2005) 30, pp. 1-46.
"1-Methylcyclopropene; Amendment to an Exemption from the Requirement of a Tolerance," Federal Register, vol. 73, No. 69 (Apr. 9, 2008) Rules and Regulations pp. 19147-19150.

(56) References Cited

OTHER PUBLICATIONS

"Ethylbloc Registration No. 71297-1 and Ethylbloc Sachet Registration No. 71297-5," Firm No. 71297, Agro Fresh Inc. Philadelphia, PA. http://ppis.ceris.purdue.edu/htbin/rnamset.com (Feb. 2, 2011) 3 pgs.
Trademark Search for "ETHYLBLOC" (Feb. 11, 2011) 2 pgs.
"ExxonMobilTM LDPE LGA 105, Low Density Polyethylene Resin," ExxonMobil Chemical, www.exxonmobilpe.com (Nov. 6, 2009) 2 pgs.
"ExxonMobilTM PP3155: Polypropylene Homopolymer ExxonMobil Chemical," IDES Prospector, IDES—The Plastics Web, www.ides.com (Nov. 6, 2009) 1 pg.
"FAO Specifications and Evaluations for Agricultural Pesticides 1-Methylcyclopropene," 2008, 30 pgs.
Neoh, Tze Loon et al. "Kinetic Study of Thermally Stimulated Dissociation of Inclusion Complex of 1-Methylcyclopropene with a-Cyclodextrin by Thermal Analysis," J. Phys. Chem. B, vol. 112, No. 49 (2008) pp. 15914-15920.
"FusabondR P MD411D," IDES Prospector, www.ides.com (Nov. 6, 2009) 1 pg.
Hotchkiss, J.H. et al. "Release of 1-Methylcyclopropene from Heat-Pressed Polymer Films," Journal of Food Science, vol. 72, No. 5, 2007. Section E: Food Engineering & Physical Properties, E330-E334.
Husken, Debby "Hydrophilic Segmented Block Copolymers Based on Poly(Ethylene Oxide)" 2006, 199 pgs.
Hwang, Suzie J. et al. "Effects of Structure of B-Cyclodextrin-Containing Polymers on Gene Delivery," Bioconjugate Chem. 12 (2001) pp. 280-290.
"IntegrateTM NE542013, Functionalized Polyolefin, Melt Index 13, Density 0.943," Equistar, Lyondell Chemical Company, Houston, Texas, http://www.Lyondell.com (Mar. 2006) 1 pg.
Jiang, Yueming et al. "Extension of the shelf life of banana fruit by 1-methylcyclopropene in combination with polyethylene bags," Postharvest Biology and Technology 16 1999) pp. 187-193.
Lee, Younsuk S. et al. "Development of a 1-Methylcyclopropene (1-MCP) Sachet Release System," Journal of Food Science, vol. 71, No. 1, (2006) Section C: Food Chemistry & Toxicology, pp. C1-C6.
"AlathonM6210High Density Polyethylene; MMW Film Grade, Melt Index 0.95, Density 0.958." Data Sheet, Lyondell Chemical Company, Houston Texas.
Macnish, Andrew J. et al. "A simple sustained release device for the ethylene binding inhibitor 1-methylcyclopropene," Institute of BioScience and Technology, Cranfield University at Silsoe, Befordshire MK45 4DT, UK. 50 pgs.
Nanthachai, Nunchanok et al. "Absorption of 1-MCP by fresh produce," Postharvest Biology and Technology, 43 (2007) pp. 291-297.
Neoh, Tze Loon et al. "Kinetics of Molecular Encapsulation of 1-Methylcyclopropene into a-Cyclodextrin," Journal of Agriculture and Food Chemistry, 55 (2007) pp. 11020-11026.
Chilean Office Action for Application No. 201603338, dated Apr. 23, 2018, 14 pages (7 pages of English Translation and 7 pages of Official Copy).
Colombian Office Action for Application No. NC2017/0000408, dated Apr. 20, 2018, 34 pages (11 pages of English Translation and 23 pages of Official Copy).
Neoh, Tze Loon et al. "Dissociation characteristics of the inclusion complex of cyclomaltohexaose (a-cyclodextrin) with 1-methylcyclopropene in response to stepwise rising relative humidity," Carbohydrate Research, 345 (2010) pp. 2085-2089.
Olabisi, Olagoke et al. "Pressure-Volume-Temperature Studies of Amorphous and Crystallizable Polymers. I. Experimental," Macromolecules 1975, 8, pp. 206-210.
Orellana, Stephanie "Ninesigma—Request #50882-1—Entrapping Gases for Agricultural Formulations," NineSigma, Inc. www.ninesigma.com (2009) 2 pgs.
"Paraffin wax," http://www.chemicalbook.com/ChemicalProductProperty_EN_CB2854418.htm (2010) 2 pgs.

Office Action dated Feb. 6, 2015 in connection with Colombian Patent Application No. 13-252.771.
Pirrung, Michael "A new idea for how anti-aging products delay ripening of fruit and wilting of flowers," www.physorg.com/news128959515.html (May 2, 2008) 2 pgs.
"PMMA (Acrylic)," PMMA Processing Guide, http://www.fastheatuk.com/mdb/pmma.html, 1 pg.
Ellis, Bryan et al. "Poly(methyl methacrylate), General," Polymers A Property Database 2nd Ed., CRC Press 2009 by Taylor and Francis Group, Boca Raton, FL pp. 726-735.
"Regulatory Note REG2004-07," Pest Management Regulator agency, 2004. 1-Methylcyclopropene, Regulatory note REG 2004-07, PMRA, Health Canada, Ottawa, Ont. pp. 1-56.
Reid, Michael S. "Use of 1-Methylcyclopropene in Ornamentals: Carnations as a Model System for Understanding Mode of Action," HortScience, vol. 43 (1) Feb. 2008, pp. 95-98.
Shkolnik, S. et al. "Radiation-Induced Grafting of Sulfonates on Polyethylene," Journal of Applied Polymer Science, vol. 27, (1982) pp. 2189-2196.
Sisler, Edward C. et al. "Competition of unsaturated compounds with ethylene for binding and action in plants," Plant Growth Regulation, 9, (1988) pp. 181-191.
Sisler, Edward C. et al. "Competition of cyclooctenes and cyclooctadienes for ethylene binding and activity in plants," Plant Growth Regulation, 9 (1990) pp. 157-164.
Sisler, Edward C. et al. "Inhibitors of ethylene responses in plants at the receptor level: Recent developments," Physiologia Plantarum, 100 (1997) pp. 577-582.
Sisler, Edward C. et al."Compounds controlling the ethylene receptor," Bot. Bull. Acad. Sin., 40 (1999) 40: 1_7 <http://ejournal.sinica.edu.tw/bbas/content/1999/1/bot41-01.html> 13 pages.
Van Velzen, E.U. Thoden "Packaging for fresh convenience food," Agrotechnology & Food Sciences Group—Wageningenur, (2008) 30 pgs.
"Fresh as the day it was harvested—luscious fruit thanks to cyclodextrins," Wacker Chemie AG, www.wacker.com, No. 5 (May 2009) 9 pgs.
Watkins, Chris B. "The use of 1-methylcyclopropene (1-MCP) on fruits and vegetables," Biotechnology Advances, 24 (2006) pp. 389-409.
Watkins, Christopher B. "Overview of 1-Methylcyclopropene Trials and Uses for Edible Horticultural Crops," 2008, 19 pgs.
Watkins, Chris B. et al. "A summary of physiological processes or disorders in fruits, vegetables and ornamental products that are delayed or decreased, increased, or unaffected by application of 1-methylcyclopropene (1-MCP)," 2005, 20 pgs.
Utto, Weerawate. "Mathamatical Modelling of Active Packaging Systems for Horticultural Products," Thesis, Massey University, New Zealand, 2008, 363 pgs.
Wooster, Jeffrey J. "Extending the Shelf-life of Fresh-cut Produce (Including the Many Advantages of AFFINITYTM Polyolefin Plastomers)," The Dow Chemical Company, 2010, 16 pgs.
Zhao, Xiao-Bin et al. "Synthesis and characterization of polymer-immobilized B-cyclodextrin with an inclusion recognition functionality," Elsevier Science B.V. Reactive Polymers 24 (1994) pp. 9-16.
Notice of Allowance dated May 14, 2013 in U.S. Appl. No. 13/574,287.
First Office Action dated May 29, 2013 in Chinese Application No. 201080060634.6.
Official Action dated Nov. 20, 2013 in Mexican Application No. MX/a/2012/006797.
Official Action dated Feb. 7, 2014 in Mexican Application No. MX/a/2012/006797.
First Office Action dated Jun. 5, 2014 in Chinese Application No. 2011104316743.
Second Office Action dated Jan. 3, 2014 in Chinese Application No. 201080060634.6.
Notice of Acceptance dated Aug. 22, 2013 in Australian Application No. 2010337146.
Office Action dated Aug. 15, 2013 in U.S. Appl. No. 13/896,803.
Office Action dated Jan. 6, 2015 in connection with Japanese Patent Application No. 2014-502539; English translation also enclosed.

(56) References Cited

OTHER PUBLICATIONS

The First Examination Report dated Jun. 6, 2014 in related New Zealand Application No. 616943.
Aug. 26, 2014 Office Action in Japanese Application No. 2012-544678. Translation included.
Aug. 26, 2014 Office Action in European Application No. 11785170.9.
Sep. 11, 2014 Office Action in Korean Application No. 10-2013-7028386. Translation included.
Sep. 12, 2014 Examination Report in Canadian Application No. 2,831,213.
Oct. 5, 2014 Translation of Notification of Defects in Israeli Application No. 228558.
Oct. 27, 2014 Office Action in Russian Application No. 2012129253. Translation included.
Nov. 5, 2014 Final Office Action in U.S. Appl. No. 12/967,226.
Maatz, Gero et al. "Cyclodextrin-induced host-guest effects of classically prepared poly(NIPAM) bearing azo-dye end groups" Beilstein Journal of Organic Chemistry. 2012, 8, 1929-1935.
Regiert, Marlies et al. "Light-Stable Vitamin E by Inclusion in y-Cyclodextrin" Sun Screens & UV Protection, Cosmetic Science Technology, 2006, p. 95.
International Preliminary Report on Patentability dated Mar. 9, 2015 in connection with International Patent Application No. PCT/US2013/072124.
Final Official Action dated May 20, 2015 in connection with Japanese Patent Application No. 2012-544678, with English Translation.
First Examination Report dated Feb. 19, 2015 in connection with related New Zealand Application No. 704723, 1 pg.
Office Action dated Mar. 5, 2015 in Russian Patent Application No. 2012129253 and English Translation, 8 pages.
Office Action dated Mar. 19, 2015 in European Patent Application No. 10795543.7, 3 pages.
Examination Report dated Apr. 1, 2015 in Canadian Patent Application No. 2831213, 3 pages.
Office Action dated May 18, 2015 in connection with Taiwanese Patent Application No. 101110340, with English Translation.
Notification of Defects dated Sep. 17, 2015 in Israeli Patent Application No. 238943.
Supplemental European Search Report dated Oct. 12, 2015 in European Patent Application No. 13828965.7.
Office Action dated Oct. 20, 2015 in Ukrainian Patent Application No. a 2013 12523, including English translation.
Office Action in Ukrainian Application No. a 2017 00715, dated Dec. 22, 2018, 6 pages of Official Copy (No English Translation Available).
Examination Report issued in New Zealand Application No. 727559, dated Oct. 5, 2018, 3 pages.
Examination Report issued in Taiwan Application No. 104120690, dated Oct. 31, 2018, 8 pages (4 pages of Official Copy and 4 pages of English Translation).
Search Report issued in Taiwan Application No. 104120690, dated Oct. 16, 2018, 2 pages (1 page Official Copy and 1 page English Translation).
Chinese Office Action issued in Application No. 2017100808182, dated Jun. 29, 2018, 16 pages (10 pages of English Translation and 6 pages of Official Copy).
Chinese Search Report issued in Application No. 2017100808182, dated Jun. 21, 2018, 2 pages (1 page Official Copy and 1 page English Translation).

* cited by examiner

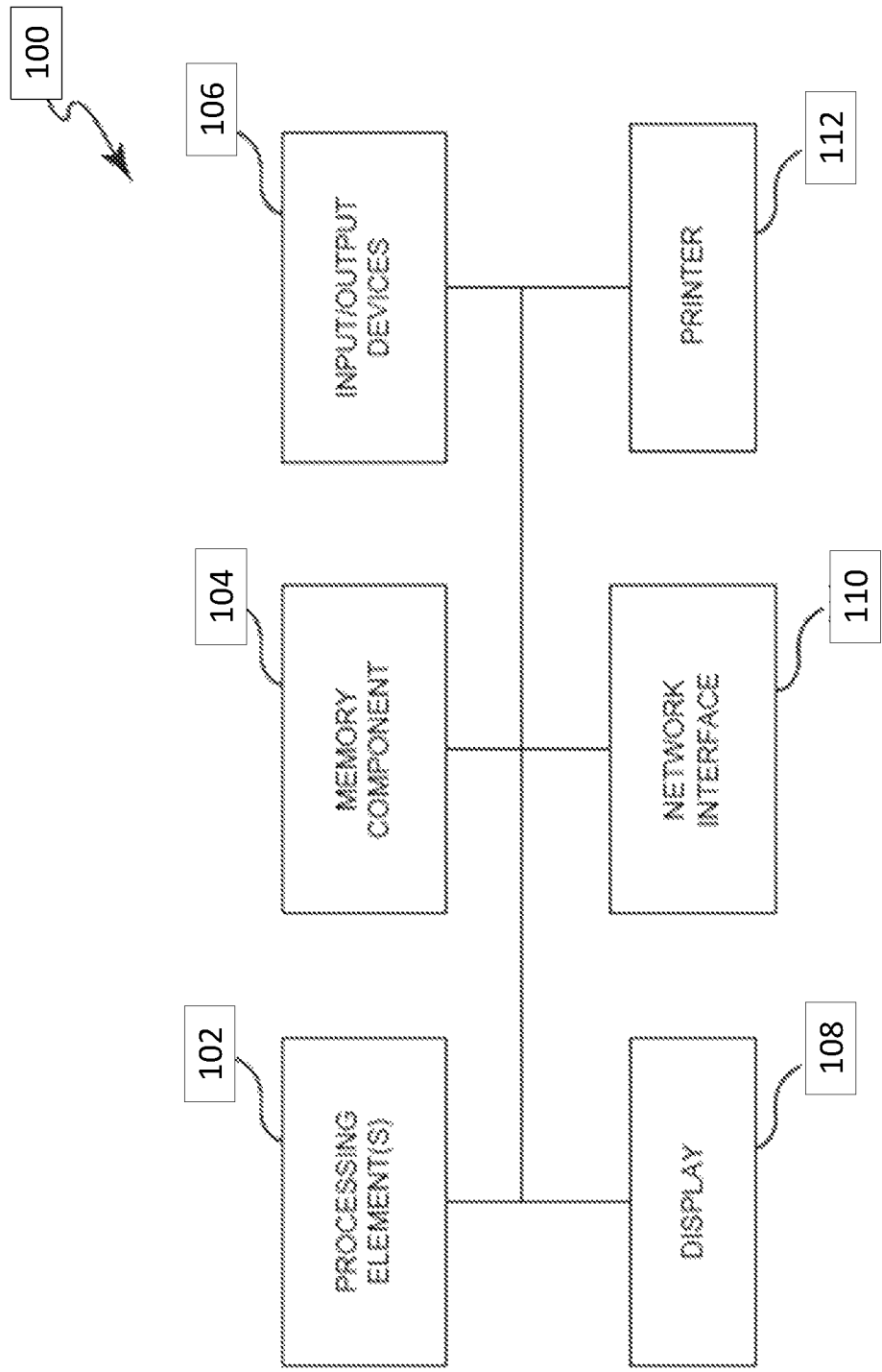

ELECTROSTATIC PRINTING OF CYCLODEXTRIN COMPOSITIONS

TECHNICAL FIELD

This disclosure relates to printing of cyclodextrin and cyclodextrin inclusion complexes onto substrates using electrostatic printing methods, and applications of the printed substrates.

BACKGROUND

Cyclodextrins are cyclic oligosaccharides of a glucopyranose, formed by the action of certain enzymes such as cyclodextrin glycosyltransferase (CGTase). Three cyclodextrins, α-cyclodextrin, β-cyclodextrin, and γ-cyclodextrin, are commercially available and consist of six, seven and eight α-1,4-linked glucopyranose units, respectively. The three-dimensional molecular configuration of these oligosaccharides is a frustoconical shape, or toroid. The specific coupling of the glucose monomers gives cyclodextrins a rigid, frustoconical molecular structure with a hollow central cavity, or pore, of a specific volume. All cyclodextrins have a relatively hydrophobic central cavity and hydrophilic outer surface. The properties of the commercially available cyclodextrins are shown in Table 1.

TABLE 1

Properties of cyclodextrin.
CYCLODEXTRIN TYPICAL PROPERTIES

| CD PROPERTIES | α-CD | β-CD | γ-CD |
|---|---|---|---|
| Degree of polymerization (n=) | 6 | 7 | 8 |
| Molecular Size (A°) | | | |
| inside diameter | 5.7 | 7.8 | 9.5 |
| outside diameter | 13.7 | 15.3 | 16.9 |
| height | 7.0 | 7.0 | 7.0 |
| Specific Rotation $[\alpha]^{25}D$ | +150.5 | +162.5 | +177.4 |
| Color of iodine complex | Blue | Yellow | Yellowish Brown |
| Solubility in Distilled water (g/100 mL) 25° C. | 14.50 | 1.85 | 23.20 |

Cyclodextrins are water soluble, as is seen in Table 1, yet have hydrophobic interiors capable of complexing with molecules having a size that fits at least partially in the toroid interior. Due to this unique structure, cyclodextrin is advantageously employed in applications where certain deleterious compounds are desirably scavenged from a surrounding environment, because the interior of the toroid allows inclusion complexes of the targeted deleterious compounds to form spontaneously.

For example, Wood et al., U.S. Pat. Nos. 5,882,565; 6,218,013; 6,306,936; 6,541,560; 6,709,746; and related publications describe scavenging malodorous and other deleterious compounds from compositions by incorporating cyclodextrin, in embodiments as a functionalized (derivative) version thereof to improve compatibility of cyclodextrin in e.g. a polymer matrix. Wood et al., U.S. Pat. Nos. 7,166,671; 7,385,004; 8,148,466; and related publications describe using cyclodextrin grafted to polymers for scavenging and barrier film applications.

A related use of cyclodextrin is as an inclusion complex thereof for subsequent release of compounds under triggering conditions and/or due to equilibration loss in an open environment. Numerous applications of cyclodextrin complexes with various medicaments, for example, are employed to deliver hydrophobic compounds to the human or animal body in a water soluble form, whereupon the cyclodextrin provides a time-release function for the medicament. The multifunctional characteristics of cyclodextrins have enabled them to be used in almost every drug delivery system, including oral, transdermal, and ocular drug delivery. The commercial viability of cyclodextrin-based oral formulations has been established with the marketing of more than 20 products worldwide. Benefits of employing cyclodextrin complexes include enhanced solubility in biological systems, enhanced bioavailability, improved drug stability, for example by prevention of drug crystallization, reduction of irritation to sensitive delivery tissues by reduction of localized drug concentrations, prevention of incompatibility between drugs and/or additives, masking of odor and taste of drugs, and improved material handling for oil or liquid drugs.

Many compounds other than medicaments are usefully incorporated into cyclodextrin complexes. Daly et al., U.S. Pat. Nos. 6,017,849 and 6,313,068 teach that 1-methylcyclopropene, effective as an olefinic inhibitor for fresh produce, is complexed with α-cyclodextrin for release in the presence of atmospheric moisture, thus triggering its release in the presence of the respiring plants to provide the benefit of the olefinic inhibition to the plant and retard the ripening thereof. Baler et al., U.S. Pat. No. 8,603,524 and Wood et al., U.S. Pat. No. 8,414,989 and related publications teach that 1-methylcyclopropene complexed with α-cyclodextrin is advantageously blended into polymer networks. Etherton et al., U.S. Pat. No. 7,019,073 teaches that fragrance compounds, antimicrobial compounds, dye compounds, and the like are advantageously complexed with cyclodextrin grafted onto polymers for controlled release, or in some cases delivery of the compounds into otherwise incompatible environments.

Given the utility of cyclodextrin for both capturing compounds from a surrounding environment and for release of compounds into a selected environment, it is desirable to deliver cyclodextrin or a complex thereof using convenient methods that are easily accessible by the user. Such delivery methods are desirably reproducible and accurate in terms of amount of cyclodextrin or cyclodextrin inclusion complex delivered. It is advantageous to provide cyclodextrin or a cyclodextrin inclusion complex using an on-demand method, such that inventories of materials are minimized.

SUMMARY

Disclosed herein is a method of printing a cyclodextrin composition onto a substrate, the method including forming an electrostatically printable composition, the composition including a polymer and one or more cyclodextrins, one or more cyclodextrin inclusion complexes, or a combination thereof; disposing the printable composition inside a cartridge, the cartridge designed and adapted to be connected to an electrostatic printer for dispensing the printable composition during electrostatic printing; connecting the cartridge to the electrostatic printer; and directing the printer to electrostatically print an image on an electrostatically printable substrate. In some embodiments, two or more cartridges are connected to the electrostatic printer, each of the two or more cartridges including a different printable composition. In some embodiments, the directing is accomplished using a computer. In some embodiments, the directing includes selecting a pattern of printing, an area of printing, or both. In some embodiments, the printable composition includes a colorant.

Also disclosed herein is an electrostatically printable composition including a particulate including a polymer and one or more cyclodextrins, one or more cyclodextrin inclusion complexes, or a combination thereof, wherein the composition is printable using an electrostatic printing method. In some embodiments, the polymer is crosslinked. In some embodiments, the composition further includes a colorant.

Also disclosed herein is a printed substrate including an electrostatically printable substrate having a first major surface including an electrostatically printable composition electrostatically printed on at least a portion of the area thereof, the printable composition including a particulate including a polymer and one or more cyclodextrins, one or more cyclodextrin inclusion complexes, or a combination thereof. In some embodiments, the printed area has a color or grayscale value that corresponds to the amount of printed composition present on the printed area. Also disclosed herein is a laminate including the printed substrate.

Also disclosed herein is an electrostatic printing system, the system including an electrostatic printer, a computer adapted to direct the printer, one or more cartridges adapted to be connected the printer for electrostatically disposing an electrostatically printable composition on an electrostatically printable substrate, the printable composition including a particulate comprising a polymer and one or more cyclodextrins, one or more cyclodextrin inclusion complexes, or a combination thereof; and one or more sheets or rolls of electrostatically printable substrate. In some embodiments, the electrostatic printer includes a fusing roller having a variable temperature, wherein the temperature is selected by the user by using the computer to direct the printer to set the fusing roller temperature. In some embodiments, the printable composition includes a colorant, and wherein the printing system further includes an electronic or printed guide displaying the correspondence of color on a printed substrate to the amount of the cyclodextrin or cyclodextrin inclusion complex that is deposited within a printed area of that color. In some embodiments, the system further includes a lamination apparatus for contacting a laminating substrate to a printed substrate to form a laminate.

Additional advantages and novel features of the invention will be set forth in part in the description that follows, and in part will become apparent to those skilled in the art upon examination of the following, or may be learned through routine experimentation upon practice of the invention.

BRIEF DESCRIPTION OF THE DRAWINGS

FIG. 1 is a diagram of a computing device that may be used in conjunction with the one or more electrostatic printers as described herein.

DETAILED DESCRIPTION

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Definitions

As used herein, the term "cyclodextrin" refers collectively and generically to any cyclodextrin species, including any of the three commercially available cyclodextrin species alpha-cyclodextrin ($\alpha$-cyclodextrin), beta-cyclodextrin ($\beta$-cyclodextrin), gamma-cyclodextrin ($\gamma$-cyclodextrin)—or any derivative thereof as defined below, and blends of two or more of these. Where specified, a particular cyclodextrin species includes derivatives thereof unless otherwise indicated.

As used herein, the term "cyclodextrin inclusion complex", "cyclodextrin complex" or "inclusion complex" means the combination of a compound and a cyclodextrin wherein at least a portion of the compound is disposed within the pore of the cyclodextrin ring. The complexed compound must satisfy the size criterion of fitting at least partially into the cyclodextrin pore to form an inclusion complex. The cyclodextrin inclusion complexes include, inherent to the formation and existence of the inclusion complex, some amount of "uncomplexed" cyclodextrin; this is because (1) in embodiments synthesis of the inclusion complex does not result in 100% formation of inclusion complex; and (2) in embodiments, the inclusion complex is in equilibrium with uncomplexed cyclodextrin/uncomplexed compound. Each combination of cyclodextrin and compound has a characteristic equilibrium associated with the cyclodextrin inclusion complex. In some embodiments, a cyclodextrin complex is denoted as "X/c/CD" wherein X is the complexed compound.

As used herein, the term "cyclodextrin derivative" means a cyclodextrin having a functional group bonded to one of the cyclodextrin glucose moiety hydroxyl groups. Some cyclodextrin derivatives are described, for example, in U.S. Pat. No. 6,709,746.

As used herein, the term "electrostatic printer" or "electrostatic printer device" means a device such as a photocopier, laser printer, or LED printer, that applies one or more materials to a substrate using electrostatic, or xerographic, technology. Such application of materials, i.e. printing, necessarily includes the computer directed solventless application of particulates to a substrate employing electrostatic attraction. Such printing can, but does not necessarily include heating the printed compositions or the printed substrates. Electrostatic printers include both sheet and roll fed printer devices.

As used herein, the term "printable composition" means a solventless particulate composition that includes at least one cyclodextrin or cyclodextrin inclusion complex species, and is capable of printing using an electrostatic printing device. In some embodiments, the printable composition is a toner composition for electrostatic printing wherein the at least one cyclodextrin or cyclodextrin inclusion complex species is added to the toner composition, for example as an admixture. Once printed on a substrate, the printable composition is a printed composition.

As used herein, the term "toner source" means a container designed to contain a toner composition within an electrostatic printer device and dispense the toner onto a substrate during electrostatic printing. The toner source is also used to store the toner compositions prior to installing them in an electrostatic printer. In many embodiments, the toner source is referred to as a "cartridge", which is a discrete container separate from the printed device but designed to be disposed in connection with the printer device and adapted to deliver a computer-directed amount of toner composition to a photoreceptor cylinder, or drum, inside the printer device. In some embodiments, the toner source is designed and adapted to receive and deliver a printable composition. In other embodiments, the toner source is not particularly adapted, and addition of a printable composition to the toner source is sufficient to enable delivery of the printable composition from the toner source when the toner source is disposed within the printer device.

As used herein, the term "printable substrate" means a material that is printable using electrostatic printing methods. In embodiments where a conventional electrostatic printer device is employed for the printing, the substrate is a sheet or film, or a roll thereof. Sheets and films are characterized as substantially planar articles having two major sides and outer edges defining a thickness. Once a printable composition is disposed on the printable substrate, the printable substrate is a printed substrate.

As used herein, the term "laminate" means a printed substrate that is further covered with a laminating substrate in a manner whereby the printed substrate and the laminating substrate are substantially adhered over at least a portion of their contacted surfaces.

As used herein, the term "laminating substrate" means a sheet or film that is adhered to a printed substrate employing an adhesive, or heat, or a combination thereof.

As used herein, the term "permeable" as applied to a printable substrate or a laminate means that the printable substrate or laminating substrate has a permeability to a compound released from a cyclodextrin inclusion complex of equal to or greater than 0.01 ($cm^3 \cdot mm/m^2 \cdot 24$ hrs·bar) at standard temperature and pressure (STP) and 0% relative humidity; or permeability to water vapor of equal to or greater than 0.1 ($g \cdot mm/m^2 \cdot 24$ hr) at 38° C. and 90% relative humidity, when measured according to ASTM D96; or permeability to $O_2$ of equal to or greater than 0.1 ($cm^3 \cdot mm/m^2 \cdot 24$ hr·bar) at 23° C. and 0% relative humidity, when measured according to ASTM D3985; or permeability to $CO_2$ of equal to or greater than 0.1 ($cm^3 \cdot mm/m^2 \cdot 24$ hr·bar) at 23° C. and 0% relative humidity, when measured according to ASTM D1434; or a combination thereof.

As used herein, the term "impermeable" as applied to a printable substrate or a laminate means that the printable substrate or laminating substrate has a permeability to a compound released from a cyclodextrin inclusion complex of less than 0.01 ($cm^3 \cdot mm/m^2 \cdot 24$ hrs·bar) at STP and 0% relative humidity; or permeability to water vapor of less than 0.1 ($g \cdot mm/m^2 \cdot 24$ hr) at 38° C. and 90% relative humidity, when measured according to ASTM D96; or permeability to $O_2$ of less than 0.1 ($cm^3 \cdot mm/m^2 \cdot 24$ hr·bar) at 23° C. and 0% relative humidity, when measured according to ASTM D3985; or permeability to $CO_2$ of less than 0.1 ($cm^3 \cdot mm/m^2 \cdot 24$ hr·bar) at 23° C. and 0% relative humidity, when measured according to ASTM D1434; or a combination thereof.

The term "produce", "fresh produce" or "produce material" includes any whole plant, plant part, such as a fruit, flower, cut flower, seed, bulb, cutting, root, leaf, flower, or other material that is actively respiring and, as a part of its maturation, generates ethylene as a maturation hormone (climacteric) or ripens without ethylene and respiration bursts (non-climacteric).

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "about 1 to about 5" and "1 to about 5" and "about 1 to 5" unless specifically limited by context.

As used herein, the word "substantially" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Intended properties include, solely by way of nonlimiting examples thereof, thickness of a printed layer or a substrate, particle size, or equilibrium constant for an inclusion complex. Intended positions include printing a material at a specified location on a substrate. The effect on methods that are modified by "substantially" include the effects caused by variation in the number or concentration of particles deposited on a substrate or the amount of inclusion complex vs. uncomplexed cyclodextrin delivered wherein the manner or degree of the effect does not negate one or more intended properties or results; and like proximate considerations. Where modified by the term "substantially" the claims appended hereto include equivalents to these types and amounts of materials.

Overview

Disclosed herein are electrostatic printing materials and methods for printing cyclodextrin and cyclodextrin inclusion complexes onto a substrate. The methods are conveniently employed in conventional manner, e.g. using a standard electrostatic printer such as a laser printer or other xerographic methods of printing. Where more than one source for printable materials is provided in the printer, it is possible to print combinations of two more cyclodextrin or cyclodextrin inclusion complexes in a single print onto a substrate. The amounts of the cyclodextrin or cyclodextrin inclusion complexes disposed on a substrate, including the individual amounts of two more cyclodextrin or cyclodextrin inclusion complexes, are easily manipulated using on-demand print technology. In this way, a user does not have to maintain an inventory of sheets or large rolls of coated materials containing cyclodextrin or cyclodextrin inclusion complexes for eventual use. Instead, the user can simply maintain one or more cartridges containing the cyclodextrin or cyclodextrin inclusion complexes for disposition within a printer, and print a selected amount of one or more cyclodextrin or cyclodextrin inclusion complexes as needed, with amounts that are easily repeated or varied according to need.

Further, where more than one source of a particular cyclodextrin or cyclodextrin inclusion complex is provided within a single printer, one or more of the sources are optionally supplied with a known concentration of colored toner particles to help identify both the type and amount of cyclodextrin or cyclodextrin inclusion complex disposed on a print. The specific color, or color saturation of a printed area, therefore, is usefully employed to identify both the types and amounts of various cyclodextrin or cyclodextrin inclusion complexes disposed on the area of the substrate. Thus, along with a supply of cyclodextrin or cyclodextrin inclusion complex in a source within a printer, the user optionally employs a chart describing the particular hue that corresponds to a specific amount of the target cyclodextrin or cyclodextrin inclusion complex.

Still further, the printed substrates having one or more cyclodextrin or cyclodextrin inclusion complexes disposed thereon are optionally laminated with an adhesive-backed laminating substrate, providing the user the ability to select a barrier layer or partial barrier that adds additional control of the release of a compound from a cyclodextrin inclusion complex, or prevents release beyond the barrier layer altogether, or provides for control of diffusion of compounds towards the cyclodextrin where they become complexed.

These and other advantages of the methods will become apparent to one of skill.

The basic steps of electrostatic printing are as follows. The printable substrates are printed using electrostatic methodology, also referred to as xerographic methodology. Electrostatic printing methods are employed in photocopying machines, laser printers, and LED printers (that employ an array of light-emitting diodes, LEDs, in place of a laser). In both sheet and roll fed printers, a revolving photoreceptor cylinder, or drum, is given a total positive charge by a charge corona wire, which is a wire with an electrical current running through it. In some embodiments, a charged roller is employed for this purpose instead of a corona wire. As the drum revolves, the laser beam or LED array directs a pattern of light across the drum surface to discharge certain points. In other words, the light "draws" an electrostatic image on the drum. The system can also work with the charges reversed, that is, a positive electrostatic image on a negative background.

After the pattern is formed, the drum is coated with positively charged toner, which is a substantially dry particulate ink material. Since it has a positive charge, the toner clings only to the negatively charged areas of the drum. For monochrome printing, the toner includes one or more thermoplastic or thermoset polymers and carbon black. For multicolor printing, individual toner cartridges supply combinations of one or more thermoplastic or thermoset polymers and colored pigments, that is, pigments that reflect cyan, magenta, and yellow wavelengths of visible light. Other additives are included, in embodiments, to enhance final adhesion of the toner to the substrate or appearance of the toner. With the toner pattern affixed thereto, the drum rolls over the printable substrate, which is moving along a belt below at the same speed as the drum is rolling. Before reaching the drum, the printable substrate is given a negative charge by the transfer corona wire or charged roller. The charge applied to the printable substrate is stronger than the negative charge of the electrostatic image on the drum, so the printable substrate attracts the toner particles from the drum. The printable substrate is moved across the drum to pick up the image pattern exactly. To keep the printable substrate from clinging to the drum, it is discharged by a detac corona wire immediately after picking up the toner. Finally, the printed substrate having the loose toner powder disposed thereon is passed through a nip having fusing rollers or a fusing bar, wherein the heat is sufficient to melt at least a portion of the polymer included in the toner particles, and press the molten materials against the printable substrate, fusing the particles to the substrate. Typically, the heater bar is set to a temperature of about 200° C. and the speed of the substrate exposes it to the heater bar for a total of about 0.1 second to 5 seconds for a section of substrate about 30 cm in length, or about 0.2 seconds to 3 seconds, or about 0.3 seconds to 1 second for a section of substrate about 30 cm in length.

The printable compositions suitably printed using electrostatic printing methods include at least a cyclodextrin or a cyclodextrin inclusion complex. In some embodiments, the cyclodextrin or cyclodextrin inclusion complex is present substantially in place of the pigment or dye present in a conventional toner composition; in other embodiments, it is present in addition to a pigment or dye. In some embodiments, the printable compositions further include a wax or a polymer in place of the polymer(s) employed in a conventional toner composition; in other embodiments, the printable compositions include a wax or a polymer in addition to the polymer(s) employed in a conventional toner composition. The methods employ any of a number of useful printable substrates, wherein the substrates are generally the same as those employed in conventional electrostatic printing methodology. Other variations of electrostatic printing methods, usefully employed to form printed substrates, and other aspects of the methods and articles formed are described below.

Printable Compositions

The printable compositions employed in conjunction with the electrostatic printing include at least a cyclodextrin or cyclodextrin inclusion complex. Any of the known cyclodextrins, including without limitation α-cyclodextrin, β-cyclodextrin, γ-cyclodextrin, cyclodextrin derivatives, polymer grafted cyclodextrins, and combinations of two or more thereof are usefully included in the printable compositions. For example, any of the cyclodextrin derivatives taught by Wood et al., U.S. Pat. Nos. 5,882,565; 6,218,013; 6,306,936; 6,541,560; 6,709,746 and related publications; and any of the grafted cyclodextrins taught by Wood et al., U.S. Pat. Nos. 7,166,671; 7,385,004; 8,148,466; and related publications are usefully included in the printable compositions.

Cyclodextrin inclusion complexes usefully included in the printable compositions include those described by Daly et. al., U.S. Pat. Nos. 6,017,849 and 6,313,068 and other ethylene receptor blocking agents complexed with cyclodextrin. UV stabilizers, thermal stabilizers, anti-oxidants, food preservatives including antimicrobial compositions for food preservation, perfumes and pheromones, and drugs for topical use by humans or animals (including antibiotics), are other examples of classes of compounds usefully included within cyclodextrin inclusion complexes incorporated in the printable compositions. Methods of making such inclusion complexes are well understood by those of skill. Such inclusion complexes are generally included in the printable compositions with the intent of eventual release, such as controlled release or triggered release, after printing. The inclusion complexes are formed with cyclodextrin, derivatives thereof, or with polymer grafted cyclodextrins.

In some embodiments, a cyclodextrin inclusion complex in the printable composition is not intended for release of the complexed compound, or release of the complexed compound is not intended to result in its subsequent loss from the printed substrate. One such application is an inclusion complex of a colorant. Cyclodextrin inclusion complexes of such colorants, for example in a polymer grafted cyclodextrin, results in ease of incorporation of the colorant into a printable composition. Subsequent triggered release of the colorant molecules, such as by heat, results in some embodiments in the release of colorant from the inclusion complex but retention of the colorant within the fused polymer on the printed substrate. In some such embodiments, the heat triggering release is provided by the fusing step in electrostatic printing. In other embodiments, the heat is an external source that causes the release of colorant to act as a thermal indicator. In other embodiments, the cyclodextrin inclusion complex itself has a characteristic color that disappears when the complex is thermally triggered to decomplex. For example, as is seen in Table 1, iodine complexes of α-, β-, and γ-cyclodextrin have characteristic colors. Incorporation of these complexes as colorants that lose their characteristic color when heated or another embodiment of a printable thermal indicator is enabled by incorporating the complexes in a printable composition.

In some embodiments, the cyclodextrin or cyclodextrin inclusion complex is provided as a printable composition in place of the toner compositions typically employed in electrostatic printing. In particular, a polymer grafted cyclodextrin or a polymer grafted cyclodextrin inclusion complex is suitably formed into particles having a particle size of 5 μm to 16 μm and the particles are useful as printable compositions. Particles of this size are formed by milling, such as jet milling as described above, or by other conventional techniques known to those of skill. In other embodiments, cyclodextrin or a cyclodextrin inclusion complex is melt blended or solution blended with a polymer capable of electrostatic printing, and the blend is formed into particles having a particle size of 5 μm to 16 μm and the particles are useful as printable compositions. In still other embodiments, cyclodextrin or a cyclodextrin inclusion complex is blended with one or more radiation polymerizable monomers and the blend is irradiated to polymerize and crosslink the monomers. Then the polymer is broken up and milled to form particles having a particle size of 5 μm to 16 μm using conventional methods.

In still other embodiments, the cyclodextrin or cyclodextrin inclusion complex, or a particulate containing the cyclodextrin or cyclodextrin complex as described above, is admixed with polymer particles commonly employed in toner compositions, and the admixture is a printable composition. In some embodiments, such admixtures include colorants; in other embodiments, the admixtures include no colorants. Useful polymer particles commonly employed in toner compositions in include styrene acrylate copolymers, styrene divinylbenzene copolymers, polyester resins, styrene butadiene copolymers, and polyolefins, wherein the polymer particles have an average particle size range of about 5 μm to 50 μm. In some embodiments where colorants are included, the cyclodextrin or cyclodextrin complex is simply admixed with a previously manufactured toner composition to form the printable composition.

In some embodiments, the cyclodextrin or cyclodextrin complex has a particle size ranging from a median size of about 5 μm to 150 μm, or about 6 μm to 100 μm, or about 6 μm to 80 μm.

In some embodiments, a particulate containing the cyclodextrin or cyclodextrin complex that is admixed with polymer particles commonly employed in toner compositions to form the printable composition includes a polymer that is grafted to the cyclodextrin or cyclodextrin complex. In some embodiments, the printable compositions further include a wax or a polymer in place of the polymer(s) employed in a conventional toner composition; in other embodiments, the printable compositions include a wax or a polymer in addition to the polymer(s) employed in a conventional toner composition. In some embodiments, a particulate containing the cyclodextrin or cyclodextrin complex that is admixed with polymer particles commonly employed in toner compositions to form the printable composition includes a wax. In particular, where a thermally triggered exclusion of a cyclodextrin inclusion complex is brought about at temperatures below the melt temperatures of many polymers, it is advantageous to blend the cyclodextrin complex into a wax that melts, for example, below 90° C.; form particulates of the wax to blend with the toner particulates, or melt blend the wax with the toner polymers before milling to form a millable toner blend.

The amount of cyclodextrin or the cyclodextrin inclusion complex included in the printable compositions is selected based on the intended end use. The amount of cyclodextrin or the cyclodextrin inclusion complex delivered by electrostatic printing is further controlled by the computer directed print density; thus, two variables are available to one of skill in selecting an amount of cyclodextrin or the cyclodextrin inclusion complex to impart to the printable compositions: the amount of cyclodextrin or the cyclodextrin inclusion complex as a weight percent of the printable composition, and the ultimate maximum print density provided on the printable substrate. In some embodiments, about 0.0001 wt % to 30 wt % cyclodextrin moieties (inclusion compounds and grafted polymers aside) are incorporated in the printable compositions, or about 0.001 wt % to 30 wt %, or about 0.001 wt % to 30 wt %, or about 0.01 wt % to 30 wt %, or about 0.1 wt % to 30 wt %, or about 0.25 wt % to 30 wt %, or about 0.50 wt % to 30 wt %, or about 0.75 wt % to 30 wt %, or about 1 wt % to 30 wt %, or about 2 wt % to 30 wt %, or about 3 wt % to 30 wt %, or about 4 wt % to 30 wt %, or about 5 wt % to 30 wt %, or about 6 wt % to 30 wt %, or about 7 wt % to 30 wt %, or about 8 wt % to 30 wt %, or about 9 wt % to 30 wt %, or about 10 wt % to 30 wt %, or about 12 wt % to 30 wt %, or about 14 wt % to 30 wt %, or about 16 wt % to 30 wt %, or about 18 wt % to 30 wt %, or about 20 wt % to 30 wt %, or about 0.0001 wt % to 28 wt %, or about 0.0001 wt % to 26 wt %, or about 0.0001 wt % to 24 wt %, or about 0.0001 wt % to 22 wt %, or about 0.0001 wt % to 20 wt %, or about 0.0001 wt % to 18 wt %, or about 0.0001 wt % to 16 wt %, or about 0.0001 wt % to 14 wt %, or about 0.0001 wt % to 12 wt %, or about 0.0001 wt % to 10 wt %, or about 0.0001 wt % to 9 wt %, or about 0.0001 wt % to 8 wt %, or about 0.0001 wt % to 7 wt %, or about 0.0001 wt % to 6 wt %, or about 0.0001 wt % to 5 wt %, or about 0.0001 wt % to 4 wt %, or about 0.0001 wt % to 3 wt %, or about 0.0001 wt % to 2 wt %, or about 0.0001 wt % to 1 wt %, or about 0.1 wt % to 15 wt %, or about 0.1 wt % to 10 wt %, or about 0.5 wt % to 15 wt %, or about 0.5 wt % to 10 wt %, or about 0.5 wt % to 7 wt %, or about 1 wt % to 7 wt % cyclodextrin moieties are incorporated in the printable compositions. The amount of cyclodextrin moieties is optimized by one of skill by taking into account the intended application, and if a release compound is employed then the speed of release of the compound in a targeted set of conditions and activity of the released compound are also taken into account.

In some embodiments, the printable compositions are formed using conventional techniques for forming dry, particulate materials that are printable using standard electrostatic printing techniques. By "dry" it is meant that the electrostatically printable particulate includes substantially no solvents. Printable composition average particle size ranges, in various embodiments, between about 4 μm to 16 μm, or about 5 μm to 16 μm, or about 6 μm to 16 μm, or about 7 μm to 16 μm, or about 8 μm to 16 μm, or about 9 μm to 16 μm, or about 10 μm to 16 μm, or about 11 μm to 16 μm, or about 12 μm to 16 μm, or about 4 μm to 15 μm, or about 4 μm to 14 μm, or about 4 μm to 13 μm, or about 4 μm to 12 μm, or about 4 μm to 11 μm, or about 4 μm to 10 μm, or about 4 μm to 9 μm, or about 4 μm to 8 μm, wherein average particle size is varied depending on the particular printer and toner source targeted. "Average particle size" means either a volume-based or weight-based average depending on the method of measurement employed; however, conventionally the average is a volume-based average. Additionally, in some embodiments, the particle size is theoretically determined by measuring volume median diameter of the particles using a Coulter counter method, and assuming all particles are spherical. Average particle sizes of about 8 µm to 10 µm are required for electrostatic printing with good resolution at 600 dots per inch (dpi). In some embodiments, the printable compositions are manufactured by compounding ingredients using melt blending; the melt mixture cools to form a slab which is crushed or pelletized, then turned into a fine powder with a controlled particle size range by air jet milling or ball milling. This process results in printable composition granules with varying sizes and aspherical shapes.

A typical process for manufacture of the printable compositions is carried out by melt-blending one or more polymers, optionally with a colorant, in an extruder to form a melt blended mixture. Melt blending is followed by reduction of particle size sufficient to obtain particles of the selected size range. Other methods are also suitably employed to form particles of a selected size range, wherein the resulting particulate functions as a "core" to receive a cyclodextrin or cyclodextrin complex-containing "shell." For example, in some embodiments, polymerization of the core polymer is carried out in an emulsion, such as a water-in-oil or an oil-in-water emulsion of monomers that are polymerized to form a latex. In such embodiments, the discontinuous phase of the latex contains the polymer, such that the discontinuous phase provides discrete polymer particles having substantially uniform size distribution and substantially spherical shape; the particles are obtained from the latex and used as the "core" particulate without further commination. In some such embodiments, the polymer is crosslinked during polymerization thereof.

In embodiments, the shell composition is formed by a high speed blending process wherein shell materials comprising, consisting essentially of, or consisting of the cyclodextrin or cyclodextrin complex are blended with the core particles to form the printable compositions.

The following melt mixing and particle size reduction methodology is optionally employed. It will be appreciated that other techniques are useful to form a polymer particulate "core" of a suitable size and composition to receive a cyclodextrin or cyclodextrin complex composition-containing "shell" substantially surrounding the core.

Examples of polymers useful to form the core particulate of the printable compositions include polyamides, epoxies, diolefins, polyesters, polyurethanes, vinyl polymers such as polyacrylates, polystyrene, or polyolefins, and polymeric esterification products of a dicarboxylic acid and a diol comprising a diphenol. For example, vinyl polymers such as styrene polymers, acrylonitrile polymers, vinyl ether polymers, acrylate and methacrylate polymers; epoxy polymers; diolefins; polyurethanes; polyamides and polyimides; polyesters such as the polymeric esterification products of a dicarboxylic acid and a diol comprising a diphenol, cross-linked polyesters; and the like are suitable for use in the printable compositions. The one or more polymers selected for the core particulate of the present invention include homopolymers or copolymers of two or more monomers, and blends of two or more polymers.

In some embodiments, one or more of the polymers are crosslinked, for example by adding a crosslinker before or during extrusion to reactively crosslink the polymer(s) during extrusion. The polymers used in printable compositions vary by manufacturer and include, in various embodiments and solely by way of example, styrene acrylate copolymers, styrene divinyl benzene copolymers, polyester resins, styrene butadiene copolymers, or another type of polymer. Colorants optionally included in the printable compositions include carbon black and ferrous oxide, where a black colorant is desired, and various organic or organometallic pigments for cyan, magenta, and yellow printable compositions, as is readily understood by one of skill in the art of colored electrostatic toner compositions. The amount of colorant is not particularly limited in the printable compositions, but in some embodiments is present in the composition at 0 to about 5 wt % of the printable composition.

Suitable vinyl monomer units in the vinyl polymers include styrene, substituted styrenes such as methylstyrene, chlorostyrene, styrene acrylates and styrene methacrylates; vinyl esters like the esters of monocarboxylic acids including methyl acrylate, ethyl acrylate, n-butyl-acrylate, isobutyl acrylate, propyl acrylate, pentyl acrylate, dodecyl acrylate, n-octyl acrylate, 2-chloroethyl acrylate, phenyl acrylate, methyl alpha chloracrylate, methyl methacrylate, ethyl methacrylate, butyl methacrylate, propyl methacrylate, and pentyl methacrylate; styrene butadienes; vinyl chloride; acrylonitrile; acrylamide; alkyl vinyl ether and the like. Further examples include p-chlorostyrene vinyl naphthalene, unsaturated mono-olefins such as ethylene, propylene, butylene and isobutylene; vinyl halides such as vinyl chloride, vinyl bromide, vinyl fluoride, vinyl acetate, vinyl propionate, vinyl benzoate, and vinyl butyrate; acrylonitrile, methacrylonitrile, acrylamide, vinyl ethers, inclusive of vinyl methyl ether, vinyl isobutyl ether, and vinyl ethyl ether; vinyl ketones inclusive of vinyl methyl ketone, vinyl hexyl ketone and methyl isopropenyl ketone; vinylidene halides such as vinylidene chloride and vinylidene chlorofluoride; N-vinyl indole, N-vinyl pyrrolidone; and the like Suitable examples of the dicarboxylic acid units in the polyesters include phthalic acid, terephthalic acid, isophthalic acid, succinic acid, glutaric acid, adipic acid, pimelic acid, suberic acid, azelaic acid, sebacic acid, maleic acid, fumaric acid, dimethyl glutaric acid, bromoadipic acids, dichloroglutaric acids, and the like; while illustrative examples of the diol units in the polyesters include ethanediol, propanediols, butanediols, pentanediols, pinacol, cyclopentanediols, hydrobenzoin, bis(hydroxyphenyl)alkanes, dihydroxybiphenyl, substituted dihydroxybiphenyls, and the like.

One exemplary polymer used to form the core of the printable composition particulates of the invention is derived from a dicarboxylic acid and a diphenol. Such polymers are illustrated in U.S. Pat. No. 3,590,000. Also, polyester resins obtained from the reaction of bisphenol A and propylene oxide, and in particular including such polyesters followed by the reaction of the resulting product with fumaric acid, and branched polyester resins resulting from the reaction of dimethylterephthalate with 1,3-butanediol, 1,2-propanediol, and pentaerythritol may also preferable be used. Further, low melting polyesters, especially those prepared by reactive extrusion, reference U.S. Pat. No. 5,227,460, can be selected as the polymer employed in the printable compositions. Other suitable polymers and core materials include styrene-methacrylate copolymers, styrenebutadiene copolymers, PLIOLITES™, and suspension polymerized styrenebutadiene copolymers described in U.S. Pat. No. 4,558,108. Polyesters containing both linear portions and cross-linked portions of the type described in U.S. Pat. No. 5,227,460 are also useful as the polymer forming the core of the printable composition particulate.

One or more of the above polymers are usefully employed in the core of the printable composition particulates. Blends and copolymers of the above, as well as crosslinked versions thereof, are usefully employed. The one or more polymers are generally present in the printable compositions in an amount of from about 50 wt % to 99.999 wt % of the printable composition, for example about 50 wt % to 99.99 wt %, or about 50 wt % to 99.9 wt %, or about 50 wt % to 99 wt %, or about 50 wt % to 98 wt %, or about 50 wt % to 97 wt %, or about 50 wt % to 96 wt %, or about 50 wt % to 95 wt %, or about 50 wt % to 94 wt %, or about 50 wt % to 93 wt %, or about 50 wt % to 92 wt %, or about 50 wt % to 91 wt %, or about 50 wt % to 90 wt %, or about 50 wt % to 89 wt %, or about 50 wt % to 88 wt %, or about 50 wt % to 87 wt %, or about 50 wt % to 86 wt %, or about 50 wt % to 85 wt %, or about 50 wt % to 84 wt %, or about 50 wt % to 83 wt %, or about 50 wt % to 82 wt %, or about 50 wt % to 81 wt %, or about 50 wt % to 80 wt %, or about 50 wt % to 79 wt %, or about 50 wt % to 78 wt %, or about 50 wt % to 77 wt %, or about 50 wt % to 76 wt %, or about 50 wt % to 75 wt %, or about 50 wt % to 74 wt %, or about 50 wt % to 73 wt %, or about 50 wt % to 72 wt %, or about 50 wt % to 71 wt %, or about 50 wt % to 70 wt %, or about 51 wt % to 99.999 wt %, or about 52 wt % to 99.999 wt %, or about 53 wt % to 99.999 wt %, or about 54 wt % to 99.999 wt %, or about 55 wt % to 99.999 wt %, or about 56 wt % to 99.999 wt %, or about 57 wt % to 99.999 wt %, or about 58 wt % to 99.999 wt %, or about 59 wt % to 99.999 wt %, or about 60 wt % to 99.999 wt %, or about 61 wt % to 99.999 wt %, or about 62 wt % to 99.999 wt %, or about 63 wt % to 99.999 wt %, or about 64 wt % to 99.999 wt %, or about 65 wt % to 99.999 wt %, or about 66 wt % to 99.999 wt %, or about 67 wt % to 99.999 wt %, or about 68 wt % to 99.999 wt %, or about 69 wt % to 99.999 wt %, or about 70 wt % to 99.999 wt %, or about 65 wt % to 99.99 wt %, or about 65 wt % to 99.9 wt %, or about 65 wt % to 99 wt %, or about 65 wt % to 98 wt %, or about 65 wt % to 97 wt %, or about 65 wt % to 96 wt %, or about 65 wt % to 95 wt %, or about 65 wt % to 92 wt %, or about 65 wt % to 90 wt %, or about 70 wt % to 99.9 wt %, or about 70 wt % to 99 wt %, or about 70 wt % to 95 wt %, or about 70 wt % to 90 wt %, or about 75 wt % to 99.9 wt %, or about 75 wt % to 99 wt %, or about 75 wt % to 95 wt %, or about 80 wt % to 99.9 wt %, or about 80 wt % to 99 wt %, or about 80 wt % to 95 wt %, or about 80 wt % to 90 wt % of the printable composition.

Optionally, one or more additional components are included in the core compositions. Where the core particulates are formed by melt blending, the additional components are suitably added before or during blending of the core materials, as determined by thermal stability of the additive(s) and selection of the formulator. In other embodiments, the one or more additional components are added as part of the shell composition (described below). One example of an additional component is a charge control additive. Suitable charge control additives include quaternary ammonium compounds and alkyl pyridinium compounds, including cetyl pyridinium halides and cetyl pyridinium tetrafluoroborates, as disclosed in U.S. Pat. No. 4,298,672, distearyl dimethyl ammonium methyl sulfate, and the like. The internal charge enhancing additives are present in the printable compositions in an amount of from 0 wt % to about 10 wt % of the printable composition, for example about 1 ppm to 5 wt % of the printable composition.

Another example of a suitable additional component is a a matrix modifier. Matrix modifiers are compounds that assist the printable composition or portions thereof to obtain a charge during printing to increase adhesion of the printable composition to the substrate during transfer to charged drum portions. Suitable matrix modifiers include, for example, 3-(4-hydroxy-3,5-dimethoxyphenyl)prop-2-enoic acid (sinapinic acid) and 2,5-dihydroxybenzoic acid. Other matrix modifiers useful in the printable compositions include aniline, 3-aminoquinoline, α-cyano-4-hydroxycinnamic acid, N,N-diethylaniline, 3-hydroxypicolinic acid (3-HPA), 3-hydroxypyridine, picolinic acid, pyridine, 2-pyridylcarbinol, 2-pyridylhydroxymethanesulfonic acid, 2-pyridinecarboxaldehyde, 2,3-pyridinedicarboxylic acid, 1-methylimidazole, triethylamine, trifluoroacetic acid, 1-butyl-3-methylimidazolium chloride, 1-butyl-3-methylimidazolium hexafluorophosphate, and 1-butyl-3-methylimidazolium tetrafluoroborate. Matrix modifiers are present in a printable composition at 0 ppm to 100 ppm based on the total weight of the printable composition, for example about 1 ppm to 100 ppm, or about 1 ppm to 90 ppm, or about 1 ppm to 80 ppm, or about 1 ppm to 70 ppm, or about 1 ppm to 60 ppm, or about 1 ppm to 50 ppm, or about 1 ppm to 45 ppm, or about 1 ppm to 40 ppm, or about 1 ppm to 35 ppm, or about 1 ppm to 30 ppm, or about 1 ppm to 25 ppm, or about 1 ppm to 20 ppm, or about 1 ppm to 15 ppm, or about 1 ppm to 10 ppm, or about 2 ppm to 100 ppm, or about 3 ppm to 100 ppm, or about 4 ppm to 100 ppm, or about 5 ppm to 100 ppm, or about 6 ppm to 100 ppm, or about 7 ppm to 100 ppm, or about 8 ppm to 100 ppm, or about 9 ppm to 100 ppm, or about 10 ppm to 100 ppm, or about 11 ppm to 100 ppm, or about 12 ppm to 100 ppm, or about 13 ppm to 100 ppm, or about 14 ppm to 100 ppm, or about 15 ppm to 100 ppm, or about 16 ppm to 100 ppm, or about 17 ppm to 100 ppm, or about 18 ppm to 100 ppm, or about 19 ppm to 100 ppm, or about 20 ppm to 100 ppm, or about 2 ppm to 50 ppm, or about 3 ppm to 40 ppm, or about 4 ppm to 30 ppm, or about 5 ppm to 25 ppm.

After the melt blending is accomplished, the blended mixture is reduced in size by any suitable comminution method including those known in the art. In some embodiments, comminution is aided by the brittleness of the melt blended polymer compositions which causes the polymer to fracture when impacted. This allows rapid particle size reduction in pulverizers or attritors such as media mills, ball mills, jet mills, hammer mills, or similar devices. Such devices when used according to standard procedures are capable of reducing typical melt blended core materials to an average particle size of about 4 μm to 30 μm, or about 4 μm to 25 μm, or about 4 μm to 20 μm, or about 4 μm to 15 μm, or about 4 μm to 10 μm. Jet mills further incorporate a classification process that sorts the core particles according to size. Core particles classified as too large are rejected by a classifier wheel and conveyed by air to the grinding zone inside the jet mill for further reduction. Core particles within the accepted range are passed onto the next toner manufacturing process.

After reduction of core particle size by grinding or pulverizing, the core particles are sorted according to size. Suitable sorting mechanisms include screens and sieves having a defined mesh size, wherein particles having a particle dimension about equal to or lesser than the mesh size will pass through the screen or sieve and the remainder of the particulate is retained by the screen or sieve. Such techniques are well understood by those of skill. Classification of the core particulate provides a classified core particulate suitable for further processing. In some embodiments, core particles finer than the selected size range are removed from the product-eligible particles. These finer particles have a significant impact on precision and accuracy regarding amount of the printable composition deposited on a substrate during printing. Core particles within the selected size range are collected and passed to process by which a shell is received by the core.

In some embodiments, a high speed blending process is employed to form the shell, which includes the cyclodextrin or cyclodextrin complex, substantially coating the core particulate to form a printable composition. In some embodiments, in addition to the cyclodextrin or cyclodextrin complex, a low-melting polymer or a wax is included in the shell composition. Low-melting shell polymers include those that have a melting point of about 40° C. to 90° C., or about 40° C. to 80° C., or about 40° C. to 70° C., or about 40° C. to 60° C.; suitable low-melting polymers include any of the polymers listed above wherein the polymer inherently or in combination with low molecular weight has a melting point in a stated range, and blends of such materials. Additional suitable low melting polymers include polyols such as polyethylene glycol having a weight average molecular weight of about 1000 g/mol to 40,000 g/mol, or about 2000 g/mol to 40,000 g/mol, or about 3000 g/mol to 40,000 g/mol, or about 4000 g/mol to 40,000 g/mol, or about 5000 g/mol to 40,000 g/mol, or about 6000 g/mol to 40,000 g/mol, or about 7000 g/mol to 40,000 g/mol, or about 8000 g/mol to 40,000 g/mol, or about 9000 g/mol to 40,000 g/mol, or about 10,000 g/mol to 40,000 g/mol, or about 1000 g/mol to 35,000 g/mol, or about 1000 g/mol to 30,000 g/mol, or about 1000 g/mol to 25,000 g/mol, or about 1000 g/mol to 20,000 g/mol, or about 1000 g/mol to 15,000 g/mol, or about 1000 g/mol to 10,000 g/mol. Waxes are a class of chemical compounds that melt at about 45° C. (113° F.) to about 90° C. to give a low viscosity liquid and are insoluble in water but soluble in organic, nonpolar solvents. Waxes are derived from plant, animal, or petroleum sources. Waxes of animal origin typically consist of wax esters derived from a variety of carboxylic acids and fatty alcohols. Suitable animal waxes include beeswax (m.p. 62-65° C.), spermaceti (occurs in large amounts in the head oil of the sperm whale), and lanolin (obtained from wool). Plant waxes are characteristic mixtures of esters and unesterified hydrocarbons. Suitable plant waxes include Carnauba wax, a hard wax obtained from the Brazilian palm *Copernicia prunifera*, candelilla wax, and ouricury wax.

Petroleum derived waxes are mixtures of alkanes in a homologous series of chain lengths. Often the waxes further include aromatic component, though in some instances the aromatic component is reduced or substantially eliminated during processing. One type of suitable petroleum wax is a paraffin wax. Paraffin waxes are mixtures of saturated n- and iso-alkanes, naphthenes, and alkyl- and naphthene-substituted aromatic compounds. The degree of branching has an important influence on the properties. Other suitable petroleum waxes include Montan wax, extracted from coal and lignite, and short-chain alkanes obtained by cracking polyethylene at 400° C. The cracked polyethylene waxes have the formula $(CH_2)_nH_2$, where n ranges between about 50 and 100. Recently, waxes having high crystalline content and high density (about 0.92 g/mL or greater) have been developed by polymerizing ethylene in the presence of a catalyst, such as a Fischer-Tropsch catalyst or other similar technology. Any of these waxes are usefully blended with at least the cyclodextrin or cyclodextrin complex to yield a shell composition.

One or more additional shell materials are usefully incorporated in the shell composition. Such additional shell materials include one or more of the following: flow agents, stabilizers, charge control additives (described above), and matrix modifiers (also described above). Flow agents include fumed silica, silicon dioxide or titanium oxide derivatives, ferric oxide, talc, hydroxy terminated polyethylenes, polyolefin waxes, including polyethylenes and polypropylenes, polymethylmethacrylate, zinc stearate, chromium oxide, aluminum oxide, titanium oxide, stearic acid, and polyvinylidene fluorides.

The printable compositions are formed by combining a core particulate with a shell material. Thus, in some embodiments, a wax or low-melting polymer and a cyclodextrin or cyclodextrin complex are suitably blended using a melt blending process, wherein the resulting blend is subjected to particle size reduction using one or more of the techniques employed to form the core particles. In other embodiments, the shell materials are simply admixed prior to addition of the shell to the core particles. In still other embodiments, the shell materials are added sequentially to the core particles during one or more high speed blending operations or other methods suitably employed to form the printable compositions.

In some embodiments, the shell materials are added to the classified core particles in a high intensity blending step. Such high intensity blending is suitably carried out using a device such as a Henschel Blender FM-10, 75, or 600 blender (obtained from Zeppelin Systems Singapore Pte Ltd. of Singapore). The high intensity blending offered by such devices serves to break agglomerated particles into the appropriate manometer size, evenly distribute the shell materials with the core particulates, and attach the shell composition to the core particulate. Shell materials become attached to the surface of the core particles during collisions between particles and with the blending tool as it rotates. Without wishing to be limited by theory, we believe that such attachment between core particles and shell materials occurs due to both mechanical impaction and electrostatic attraction. The amount of time used for the blending process plus the intensity determines how much energy is applied during the blending process. "Intensity" can be effectively measured by reference to the power consumed by the blending motor per unit mass of blended core and shell materials. In some embodiments, blending times using a high intensity blending tool such as those described above range from about 1 minute to 30 minutes per batch of 1-500 kg. In some embodiments, blending speed and times are increased in order to assure that multiple layers of shell materials become attached to the core particles. Higher blending speed and additional time is required in some embodiments. In some embodiments, the intensity or time of the blending is limited by the need to avoid friction sufficient to heat the shell composition above the melt temperature of the wax employed in the composition.

The high intensity blending causes application of the shell material to the core particles. In embodiments, the application of the shell to the surface of the core particulate results coverage of about 50% to 250% of the theoretical surface area of the core particles, or about 75% to 250%, or about 100% to 250%, or about 125% to 250%, or about 150% to 250%, or about 175% to 250%, or about 200% to 250%, or about 50% to 225%, or about 50% to 200%, or about 50% to 175%, or about 50% to 150%, or about 50% to 125%, or about 50% to 100%, or about 50% to 75%, or about 100% to 200% of the theoretical surface area of the core particles. Theoretical surface area is calculated by determining the median diameter of the core particles using a standard Coulter counter method and assuming all particles are spherical; and further wherein the shell material is distributed as primary particles in a closed hexagonal packed structure on the core particle surface.

In some embodiments, two or more shell materials are added sequentially during the high speed blending process. For example, in embodiments a cyclodextrin or cyclodextrin complex is blended with the core particulate in a first blending step, then a low-melting polymer or wax is added in a second blending step to result in a core-CD-shell particulate wherein the cyclodextrin or cyclodextrin complex is denoted CD. More than two such materials, or repeated additions of aliquots of CD and low-melting polymer, optionally with one or more additional materials included in each addition, are suitably added to the core particulate without limitation to build a suitable electrostatically printable composition of the desired average particle size.

After the high intensity blending, the process of manufacturing the printable compositions is completed by a screening process to remove agglomerated particles and other particulates lying outside the selected average particle size range. Such screening techniques are described above; such techniques are also suitably employed to classify printable compositions of suitable average particle size. Suitable average particle size differs depending on the electrostatic printer device and delivery mechanisms provided by one or more containers (toner sources) used to house the printable compositions as described below.

In some embodiments, the printable compositions are stored in containers that are toner sources. Toner sources are airtight containers that maintain their contents in a substantially dry state and further wherein the small particles employed in toner compositions are substantially prevented from becoming airborne. In some such embodiments, the toner sources are cartridges that are designed and adapted to be disposed directly within a specific printer. In such embodiments, the printable compositions are simply added to the cartridge, wherein the printable composition is delivered in a controlled fashion to the photoreceptor drum on demand and as directed by a computer. The sealed configuration of cartridges as discrete containers is highly advantageous for storage and printing of printable compositions including water sensitive cyclodextrin inclusion complexes. Water sensitive cyclodextrin complexes include complexes wherein the included compound is released from the $\alpha$-cyclodextrin torus by the action of water. One highly water sensitive cyclodextrin complex is 1-methylcyclopropene/c/$\alpha$-CD (1-MCP/c/$\alpha$-CD), where it is well documented that water in both liquid and vapor form displaces—thereby ejecting—1-MCP from the complex. Since the use of water as a trigger for ejection of compounds is useful in many applications where a cyclodextrin complex is employed, it is desirable in such applications to maintain the cyclodextrin complex in a dry state until it is disposed at the targeted site where ejection is desired. Thus, the ability to store such cyclodextrin complexes in a dry, sealed container until the print on-demand is supplied to the substrate is highly advantageous feature of the electrostatic printing method. In this manner, the yield of complex-bearing cyclodextrin is maximized even over very long periods of time, such as one year up to 10 years or even more, and without taking any special precautions.

In the case of 1-MCP/c/CD, the ability to store the complex in a dry state for extended periods of time is not only advantageous for yield purposes, it is critical for safety purposes to avoid building up 1-MCP in a non-complexed state. It is established that 1-MCP, when accumulated in an enclosed area, is highly susceptible to violent autopolymerization. Thus, where a 1-MCP/c/CD complex is present in an enclosed container, it is critical to avoid the release of appreciable amounts of 1-MCP from the complex, lest the contents of the container detonate. The sealed, dry environment presented within the cartridges provides an excellent storage-stable container for 1-MCP/c/CD. Further, the container is then disposed within the printer for direct delivery of the printable composition containing the inclusion complex to the photoreceptor drum and then the substrate, avoiding the need for further handling by the user or prolonged exposure to atmospheric moisture prior to final disposition of the complex on the printable substrate.

Other inclusion complexes benefit similarly from the sealed toner sources as storage containers to preserve and protect the complexes until direct delivery of the printable compositions to the desired substrate. However, in the case of 1-MCP, the advantage is even more critical because the secure storage of the complex in a sealed dry environment, with exposure of only the delivered amount of complex to the target substrate, offers a significant safety advantage over every method known for delivery of the complex to a targeted substrate.

Printable Substrates

In embodiments, the printable compositions are electrostatically printed onto any one or more of a number of useful printable substrates. In some embodiments, the substrates are the same as those employed in conventional electrostatic printing methodology. Suitable printable substrates are planar, having two major sides and an outer edge defining a thickness of about 12 μm to 1 mm thick, and are sufficiently flexible to withstand 180° passage around a roller having a diameter of an inch or less without substantial permanent deformation. In embodiments, the printable substrates include a paper or another nonwoven material, or a solid polymeric sheet including a polyolefin, a polyamide, a polyester, polyvinylchloride, polyvinylidene chloride, or a polymer coated on a paper. Papers suitably employed include newspaper stock, kraft paper, standard office copier or printer paper, and specialty papers having various coatings thereon for printing purposes, ornamental purposes, or both. Printing purposes include electrostatic printing purposes or other printing purposes, such as inkjet printing purposes. In some embodiments, the printable substrate includes an adhesive backing that is typically covered by a removable liner prior to and during printing. In some embodiments, the adhesive backed printable substrate is usefully employed as labelstock. In some such embodiments, the labelstock is converted prior to printing into scored sections of a sheet that are peeled off the liner after printing.

The printable substrates usefully employed in conjunction with the methods include both sheet and roll forms, wherein sheets are usefully employed in some embodiments for letter size printing, such as a printer that includes a tray for 21.6 cm×27.9 cm (8.5 in.×11 in.) office paper or other sheets and further includes a mechanism to pick and place an individual sheet from a stack into the printer mechanism for each individual sheet print. Sheet sizes other than 21.6 cm×27.9 cm are accommodated by many such printers; thus, the size of sheets employed as printable substrates are limited only with respect to the particular printer design employed in conjunction with the methods.

Printable substrates in roll form are usefully employed, for example, where a high volume of printed substrates are generated in a short period of time or where variable size prints are required. Additionally, where a large volume of printable substrate per print is required, wide format printers almost universally are roll fed. Or have the capability of roll feed. Roll fed printers employ printable substrates defined by the width of the roll and are supplied in various lengths suitable for generating multiple sections of selected lengths. Roll fed printers are available in small formats, such as to print individual labels having widths of 1 cm, up to 152 cm (about 60 inches) or even larger widths for wide format printing. Rolls of any of the materials recited above are usefully employed in conjunction with roll fed printers. In many embodiments, the roll fed printers further include a mechanism to slice a selected printed length from the roll to provide a finished printed product.

Methods of Printing

While the methods employed in electrostatically printing the printable compositions are in some embodiments identical to the methods carried out by employing a conventional type of electrostatic printer in a conventional manner, in other embodiments differences are presented in the mechanics of the printing methodology. Specifically, in some embodiments, the fusing rollers through which the printed substrate is passed to heat the printed compositions and fuse the particles to the substrate is either heated to a lower set temperature than employed in conventional toner composition printing, or is not heated at all.

Thus, in some embodiments, the heater rollers are heated to a temperature of less than 200° C. For example, the fusing rollers in some embodiments are set to a temperature of about 80° C. to 200° C., for example about 100° C. to 190° C., or about 110° C. to 180° C., or about 120° C. to 170° C., or about 130° C. to 160° C., or about 130° C. to 150° C. In other embodiments, the roller is not heated at all, but rather is simply a physical pressure point that serves to press the printed composition against the printed substrate to affix the printed composition thereto. For example, where the printable substrate includes cyclodextrin or a cyclodextrin complex in a particle including a wax, the rollers are not heated or are heated to a temperature of about 100° C. or less, such as 60° C. to 90° C. In other embodiments, the printable substrate includes a low-melting polymer, and the "fusing" is accomplished by softening the surface of the printed substrate while pushing the printed composition into the substrate surface. For example, a low-density polyethylene coated paper is suitably employed in some such embodiments, wherein the temperature of the fusing rollers is selected to soften the polyethylene, allowing the printed composition to become embedded therein due to pressure applied by the rollers.

The use of low temperature fusing rollers enables the use of printable compositions including cyclodextrin complexes wherein heat triggers exclusion of the included compound. For example, it is known that loss of 1-MCP from 1-MCP/c/α-CD is triggered at temperatures as low as 90° C.; thus, providing a wax-based printable composition, or employing a low-melting printable substrate surface in conjunction with maintaining fusing rollers at a temperature of about 90° C. or less enables the electrostatic printing of printable compositions having 1-MCP/c/α-CD without suffering undue loss of 1-MCP during the printing operation. Similarly, fragrance compounds or other molecules having some vapor pressure at common ambient temperatures (e.g. 20° C.-40° C.) wherein their cyclodextrin inclusion complexes are useful for printing purposes benefit from the use of low temperature electrostatic printing methods. Such methods include the use of wax based or other low-melting materials in the printable composition, coupled with unfusing rollers or rollers maintained at a temperature beneath 200° C.

As is disclosed above, the electrostatic printer devices useful in conjunction with the printable compositions are in communication with one or more computers. FIG. 1 is a simplified block diagram of a computing device that may be used in conjunction with the one or more printers described herein. With reference to FIG. 1, the computer 100 may include one or more processing elements 102, one or more memory components 104, one or more input/output devices 106, a display 108, and/or a network interface 110. Each of the elements of the computer 100 may be in communication with one another or may be in communication with select elements, such as the processing element 102, and not in communication with other elements.

Additionally, the computer 100 may be integrated with select components and may be physically separated from others but be in communication therewith through a network (e.g., WiFi, Internet, Bluetooth, Ethernet, Universal Serial Bus, or the like) or other communication mechanism. For example, the display 108 may be physically separated from the computer 100 but be in communication with the processing elements 102 and other components of the computer 100. Similarly, the computer 100 may be in communication with the printer 112, which is similar to the electrostatic printer devices disclosed herein.

With continued reference to FIG. 1, the one or more processing elements 102 may be substantially any device capable of processing, receiving, and/or transmitting instructions. For example, the one or more processing elements 102 may be a microprocessor or microcomputer. Additionally, it should be noted that in some embodiments select components of the computer 100 may be controlled by a first processor and other components of the computer 100 may be controlled by a second processor where the first and second processors may or may not be in communication with one another.

The one or more memory components 104 store electronic data that may be utilized by the computer 100. For example, the memory component 104 may store electrical data or content, such as or one or more audio files, video files, document files, and so on, corresponding to various applications. The memory component 104 may be, for example, non-volatile storage, a magnetic storage medium, optical storage medium, read only memory, random access memory, erasable programmable memory, or flash memory.

The network interface 110 facilities communication between the computer 100, one or more electrostatic printers 112, as well as other electronic devices (e.g., other computers). For example, the network interface 110 may receive data from one or more electronic components or devices, as well as facilitate transmission of data to one or more electronic components or devices including an electrostatic printing device. The network interface 110 may be used to receive data from a network, or may be used to send and transmit electronic signals via a wireless or wired connection (Internet, WiFi, Bluetooth, and Ethernet being a few examples). In some embodiments the network interface 110 may support multiple network or communication mechanisms. For example, the network interface 110 may pair with another device over a Bluetooth network to transfer signals to the other device while simultaneously receiving data from a WiFi or other network.

The display 108 may be integrated with the computer 100, such as a tablet computer, or may be separate from the computer 100, such as a stand-alone monitor. The display 108 displays one or more output images and/or videos and is used to provide output to a user. The display 108 may be substantially any type of display screen such as a liquid crystal display, plasma display, light emitting diode screen, or the like. Additionally, in some embodiments the display 108 may include one or more input components. For example, the display 108 may include one or more sensors to detect input signals as a user touches the display 108 either through a finger or an input device such as a stylus.

The input/output devices 106 are used to provide input to the computer 100. For example, the input/output devices 106 may include a keyboard, a mouse, a joystick, stylus, track pad, handheld controller, or the like. Additionally, the input/output devices 106 may include one or more sensors, such as image sensors, capacitive sensors, or the like. The input/output devices 106 are in communication with the display 108 and the processing elements 102 and enable a user to provide input to the computer 100.

Transmission of data from the computer 100 to an electrostatic printer device 112 includes, in embodiments, a raster image processor (RIP). Raster image processing is the process and the means of turning vector digital information such as a PostScript file into a high-resolution raster image. The RIP produces a raster image also known as a bitmap. The bitmap is then sent to the electrostatic printing device for output. The input may be a page description in a high-level page description language such as PostScript, Portable Document Format, XPS or another bitmap of higher or lower resolution than the output device. In the latter case, the RIP applies either smoothing or interpolation algorithms to the input bitmap to generate the output bitmap. A RIP can be implemented either as a software component of an operating system or as a firmware program executed on a microprocessor inside a printer, though for high-end typesetting, standalone hardware RIPs are sometimes used.

A RIP chip is used in electrostatic printers to communicate raster images to the laser or LED array. Raster image processing generally includes three stages: interpretation, rendering, and screening. During the screening step, a continuous-tone bitmap is converted into a halftone (pattern of dots). Dot placement is precisely controlled by sophisticated mathematical algorithms, wherein "dots" are applied as laser or LED irradiation to the photoreceptor drum.

In embodiments, the concentration of the selected cyclodextrin or cyclodextrin complex in the printable composition is known; and the print density selected by a user and input to the computer to communicate to the printer corresponds to an amount of cyclodextrin or cyclodextrin inclusion complex in a selected area. Taking the simplest example of this method of printing, a single-cartridge electrostatic printer, the same as or similar to a monochrome (grayscale) type laser printer, is employed in connection with a printable composition. Even where the printable composition has no pigment, the cartridge delivers a printed composition density as selected by the user by inputting the corresponding density direction to the computer, further as interpreted by the RIP. In embodiments, the print density is visually represented to the user on the display as a grayscale image. The user selects an area of a printable substrate to print and the darkness of the printed area. The darkness selected by the user corresponds to the amount of printable composition printed to the printable substrate in the selected area. As represented by the display, a white area is an area where no printable composition is deposited on the printable substrate; a black or gray area includes the printable composition; and a black area is an area where the maximum density of printable composition is deposited on the substrate. In some embodiments, the printed area is a block or some other solid area. In other embodiments the printed area is a regular or irregular pattern or set of shapes; the selected area is not particularly limited and multiple areas are selected in some embodiments. Similarly, the printed area(s) are a single shade of gray, black, or a gradient of shades. Since the concentration of cyclodextrin or cyclodextrin complex in the printable composition is known, and it is known or easily determined how much printable composition is printed at the maximum printed density—that is, areas corresponding to "black" as represented to the user by the display—it is easily determined exactly how much cyclodextrin or cyclodextrin inclusion complex is deposited by any user selected pattern, gradient, and the like.

Thus, in a representative embodiment, an algorithm including the concentration information for cyclodextrin or cyclodextrin complex in the printable compositions in a cartridge is included in the RIP protocol or as a separate algorithm, and the user is enabled to select the exact amount of cyclodextrin or cyclodextrin complex deposited on the printable substrate. In some embodiments, the user selects the amount of cyclodextrin or cyclodextrin complex desired in a selected area, and the algorithm selects the proper print density to deliver the selected amount of cyclodextrin or cyclodextrin complex to the area. In other embodiments, the user selects an area and a pattern or grayscale image, and the input from the user is employed to calculate the amount of cyclodextrin or cyclodextrin complex that will be deposited. This information is supplied via the display to the user prior to the user executing the print command.

In some embodiments, the printable compositions include a pigment. In such embodiments, the user also has the option of determining the location of the deposited cyclodextrin or cyclodextrin complex after the print is made, and even how much cyclodextrin or cyclodextrin complex was deposited. In such embodiments, a color analyzer or some other instrument capable of measuring the grayscale image as a quantitative measurement is suitably employed to measure the amount of printable composition deposited in an area. If the amount of printed area is known, the exact amount of cyclodextrin or cyclodextrin complex is easily calculated.

In still other embodiments, the printer system employs more than one cartridge, for example four print cartridges. Four-cartridge printer systems are commonly designed for color printing, for example, wherein the toner compositions employed therein include black, cyan, magenta, and yellow pigments. In such embodiments, four different cyclodextrin or cyclodextrin complexes are suitably employed in four different printable compositions. The RIP is then directed to form a "multicolor" image that in fact represents an individually selected collection of cyclodextrins or cyclodextrin complexes in each "image" wherein each individual composition is delivered to a printable substrate in a selected amount, as in the simple grayscale image selection described above.

In some embodiments, similarly to the simple grayscale image selection described above, the printable compositions included in printer systems having two or more cartridges include pigments. In some such embodiments, the printer system has four cartridges having four different printable compositions, that is, four different cyclodextrins or cyclodextrin complexes, wherein the printable compositions are individually identified by having a different pigment in each cartridge. In embodiments, the four pigments are black, cyan, magenta, and yellow; in other embodiments the pigments are other colors, such as red, blue, green, orange, violet, or the like and are not particularly limited. The pigments serve to identify what areas of the printed substrate have which cyclodextrin or cyclodextrin complexes printed thereon. Where the pigments are black, cyan, magenta, and yellow, a mixed image is also identifiable as having a characteristic color representing a characteristic mix of printable compositions. As is described above for the simple case of grayscale, a color analyzer such as an analyzer capable of measuring L*a*b* colorspace can provide identification of the color that in turn is useful by the user to determine both the type(s) and the amount(s) of cyclodextrin or cyclodextrin complex(es) in a particular area of the printed substrate.

Printing Systems

Systems employed by a user to form a printed substrate includes at least an electrostatic printer, a computer adapted to direct the printer, one or more cartridges including a printable composition and adapted to be mounted on the printer for electrostatically disposing the printable composition on a printable substrate, and one or more sheets or rolls of printable substrate.

In some embodiments, each of the one or more cartridges includes a label with information regarding the type and amount of cyclodextrin, cyclodextrin complex, or combination thereof present in the printable composition.

In some embodiments, the printer is characterized by a fusing roller having a variable temperature, wherein the temperature is selected by the user, using the computer to provide instructions to the printer. In some such embodiments, the user is able to instruct the printer to shut off the heat source within the fusing roller.

In some embodiments where the printable compositions include colorant, an electronic or printed guide to color correspondence to the amount of the cyclodextrin or cyclodextrin inclusion complex that is deposited on a printable substrate is supplied to the user of an electrostatic printing system.

In some embodiments, the system further includes a lamination apparatus for contacting a laminating substrate to a printed substrate to form a laminate.

Applications of Printed Substrates

Some applications of some printable substrates are described below. It will be understood that these exemplary embodiments are only meant to be representative of the entirety of what is available to an end user equipped with an electrostatic printer connected to a computer, a supply of the desired printable composition in one or more cartridges designed to print the printable compositions when disposed in the printer, and a supply of the desired printable substrate. Many other embodiments are possible and will be easily envisioned as equivalents of the embodiments described herein.

Further, it is a feature of the methods of invention that, since the cartridges commonly employed in laser printers or LED printers are easily interchanged, a nearly limitless supply of various printable compositions including cyclodextrin, cyclodextrin inclusion complexes, or both are easily stored in cartridges that are mounted on an electrostatic printer when needed. Since the printable compositions are maintained in a dry state, even inclusion complexes with water triggered release of compounds are stored under shelf stable conditions and are not e.g. repeatedly exposed to atmospheric humidity via multiple openings of a standard container. Further, a broad range of printable substrates are employed to provide variable functionality to the printed substrates. Using the printable compositions and printable substrates as described, no inventory in the form of printed substrates need be stored at the location of use; rather, a printed substrate is simply printed on-demand. This feature makes the flexibility of the methods in generating a customized set of materials even more advantageous.

The printed substrates bearing one or more cyclodextrins, for example, are useful in some embodiments to scavenge malodor or off-flavor compounds from the interior of comestibles packages, musty odors from clothing storage areas, and the like. Because cyclodextrins in general are GRAS compounds, printed substrates having cyclodextrin included on the printed first major side are conveniently included even in the interior of food packaging to scavenge deleterious gaseous or liquid compounds therefrom.

Further, the on-demand production of substrates bearing one or more cyclodextrin inclusion complexes is advantageous for making dermal patches for release of medicaments from a medicament/c/CD bearing printed substrate, slow-releasing fragrance sheets from a fragrance/c/CD bearing printed substrate, and 1-MCP releasing sheets from a 1-MCP/c/CD bearing printed substrate for inclusion in fresh produce packaging. In some embodiments, more than one such cyclodextrin inclusion complex is suitably printed on the substrate using a multi-cartridge printer. Examples of useful combinations include multiple medicaments for dermal delivery, such as an anti-inflammatory/c/CD and an antibiotic/c/CD; or combinations of 1-MCP/c/CD with a fungicide/c/CD, an insecticide/c/CD, an antibacterial/c/CD, or two or more thereof on a single printable substrate; such on-demand and selected levels achievable for each composition printed using the methods disclosed above result in a flexible system to address multiple types of fresh produce. Some types of fresh produce require only minute amounts of 1-MCP but are prone to fungus formation, for example; in such cases, the printing methods, as described above, are usefully employed to print a low concentration of 1-MCP/c/CD together with a greater amount of fungicide/c/CD.

Dermal patches including one or more medicaments in cyclodextrin complexes are suitably stuck to the skin by, for example, providing a water-activated adhesive on the printable surface thereof, and applying water to the patch to adhere it to the skin. In some embodiments, the water triggers the release of one or more of the medicaments from the inclusion complex thereof and allows effective transfer of the compound(s) to the skin surface. In a related embodiment, a water- or saliva-soluble film is printed with one or more medicaments and the printed substrate is used as a buccal delivery vehicle, wherein the medicament(s) are dispensed through the oral mucosa as the film dissolves.

In some embodiments, printed substrates having cyclodextrin or a cyclodextrin complex printed on a first major side thereof have an adhesive disposed on at least a portion of the second major side thereof. Such printed substrates are useful for many applications. Applications of such printable substrates include printing an antimicrobial/c/CD on the first major side thereof followed by adhesion of the printed substrate to a countertop, as a die-cut set of stickers on keyboard buttons, onto door handles, and the like for slow release of the antimicrobial. Similarly, an adhesive-bearing printed substrate including a fragrance/c/CD inclusion complex is conveniently used by sticking the substrate or a portion thereof to the inside of a clothing drawer, on an interior surface of a closet, on a bathroom surface, or the like for slow release of fragrance molecules. Similarly, an adhesive-bearing printed substrate including a cyclodextrin is conveniently used by sticking the substrate or a portion thereof to the inside of a clothing drawer, on an interior surface of a closet, on a bathroom surface, or the like to scavenge malodorous compounds.

In some embodiments, an adhesive-bearing printed substrate including a 1-MCP/c/CD inclusion complex is conveniently used by sticking the printed substrate or a portion thereof to the inside of a fresh produce package, on the surface of a cardboard box or open carton containing fresh produce, inside a modified atmosphere package or a controlled atmosphere package, or the like for slow release of 1-MCP in proximity to the produce for effective prevention of ripening. Amounts of 1-MCP that are effective to prevent or slow ripening of fresh produce vary significantly from plant to plant; using the on-demand and highly variable amount of 1-MCP/c/CD printable using the methods described above, a broad array of plant types are easily addressed using a single printer, print cartridge having 1-MCP/c/CD, and printable substrate. These substrates can further have one or more pesticides, fungicides, preservatives, antimicrobials, etc. applied thereto using a multiple-cartridge printer wherein additional cartridges contain such compounds as part of cyclodextrin inclusion complexes. In this manner, an adhesive article having a customized of compounds in customized amounts are easily made for use with individual types and amounts of produce.

Useful in some embodiments as printable substrates are peel-off, die-cut stickers commonly sold for printing applications by companies such as Avery Dennison Corporation of Glendale, Calif. and others. Alternatively, a portion is cut from the printed substrate by the user, for example using scissors or a die cutter. In this manner, very small portions of 8.5"×11" or smaller sheets, or long sheets up to 60" wide, are both easily generated using the printing methods and printable compositions in conjunction with a broad array of printable substrates, and are easily used by sticking the substrate to a selected surface.

In some embodiments, a printed substrate printed on the first major side of the printable substrate with one or more cyclodextrin or cyclodextrin inclusion complexes is laminated, wherein the laminating substrate is disposed over the first major side thereof. Such embodiments are useful, for example, with or without an adhesive backing on the second side thereof. The laminating substrate is applied using an adhesive in some embodiments; for example, printed substrates up to 12" wide are conveniently laminated using a SCOTCH® Laminating Dispenser and adhesive-backed laminating substrate dispensed in roll form, for example from Cartridge LS1000 or DL1005 (all available from the 3M Company of Maplewood, Minn.). Thermal laminators are also available and useful in some embodiments; examples include the 12" wide GBC Ultima 35 EZload Thermal Roll Laminator (available from General Binding Corporation of Lincolnshire, Ill.).

Lamination of printed substrates offers a dual permeability sheet to be formed, wherein the composition of the printed substrate and the lamination substrate are selected for permeability. Thus, in some embodiments, the amount of triggering compounds, such as water, that diffuse through the laminate are easily controlled. In other embodiments, the amount of included compound that is able to diffuse out of the laminate is easily controlled. In still other embodiments, the diffusion through the laminate of a compound to be scavenged by cyclodextrin is easily controlled.

In one representative embodiment, a 1-MCP/c/CD complex is suitably printed using an electrostatic printer, wherein no heat is applied during the printing process; thus, the 1-MCP/c/CD is not triggered to release 1-MCP by application of heat. The printed sheet is immediately laminated using an adhesive laminating substrate. In such embodiments, the printed substrate and the laminating substrate are both selected for permeability of water vapor and 1-MCP. Using films of known permeability, the amount of water that is available to trigger 1-MCP loss from the complex, and the amount of 1-MCP that is able to leave the laminate are both easily controlled. For example, in some embodiments, the printable substrate is permeable to 1-MCP and impermeable to water, and the laminating substrate is permeable to water and not permeable to 1-MCP. In such embodiments the laminate provides a unidirectional flow of triggering compound and loss compound. In other embodiments, the printed substrate is impermeable to both 1-MCP and water, and the laminating substrate is permeable to both 1-MCP and water. In some such embodiments, the printed substrate further includes an adhesive backing, similar to the embodiments described above, and the laminate is suitably adhered to a surface during use.

In still other embodiments, both the printed substrate and the laminating substrate are permeable to 1-MCP and impermeable to water. In such embodiments, heat is the sole trigger for release of 1-MCP, particularly if the edges are sealed, or the adhesive used in the laminating substrate is impermeable to water, or both. Use of such a laminate includes the ability to provide a heat source, such as an infrared light source, physically contacted heat source, and the like to heat all or a portion of the laminate to 90° C. or greater, whereupon release of 1-MCP is triggered and the 1-MCP diffuses out of the laminate.

Similar uses are envisioned with cyclodextrin inclusion complexes including fragrances, medicaments, preservative compounds, and antimicrobials, wherein the laminate controls, or allows the user to control the triggered release of the compound or the diffusion of the compound out of the laminate after release.

Other uses of laminates include barrier materials. In such embodiments, a laminate having cyclodextrin disposed therein is an effective barrier layer or scavenging substrate. Such laminates are also usefully employed in forming containers for comestibles. For example, paperboard milk or juice containers are typically layered constructions, wherein one or more plastic films are incorporated. Laminates are usefully employed as a film component in such constructions, where they usefully scavenge off-flavor and off-odor compounds. Permeability of one or both of the printed substrate and the laminating substrate are selected for permeability of a compound to be scavenged. In some embodiments, the printed substrate further includes an adhesive backing, similar to the embodiments described above, and the laminate is suitably adhered to a surface during use.

EXPERIMENTAL SECTION

Example 1

An inclusion complex of 1-butene and α-cyclodextrin was formed using the technique described by Neoh, T. L. et al., J. Agric. Food Chem. 2007, 55, 11020-11026 *"Kinetics of Molecular Encapsulation of* 1-*Methylcyclopropene into* α-*Cyclodextrin"* except that 1-butene (99.0% pure, Scott Specialty Gases, Plumsteadville, Pa.; also known as Air Liquide America Specialty Gases LLC) was bubbled through a saturated α-cyclodextrin solution instead of 1-MCP. A precipitate was formed during the process, which was collected by filtering through a 10 micron fritted filter, washed with 0° C. to assist removing residual complex surface water, and dried at ambient temperature at 0.1 mm Hg for about 24 hours. The inclusion complex was termed "1-butene/c/α-CD."

The 1-butene/c/α-CD was analyzed by adding 100 mg of the collected and dried precipitate to a 250 mL glass bottle equipped with a septum cap, taking care to ensure that no powder adheres to the walls of the bottle. After about 1 hour, 250 µL of headspace gas was removed from the bottle using a six port, two-position gas sampling valve (Valco #EC6W) interfaced directly to a gas chromatograph (GC; Hewlett Packard 5890) using a RTx-5 GC column, 30 m×0.25 mm I.D., 0.25 µm film (obtained from Restek, Inc., of Bellefonte, Pa.) and equipped with flame ionization detector (FID). No measurable concentration of 1-butene was detected because of the lack of humidity (water vapor) in the headspace of the bottle. Then 3 mL of water was injected into the bottle through the septum, and the bottle is placed on a mechanical shaker and mixed vigorously for about 1 hour.

After the shaking, 250 µL of the headspace gas is removed and added to an empty 250 mL bottle equipped with a septum cap, wherein the interior of the bottle was purged with nitrogen gas. The headspace concentration of 1-butene was quantified in the second bottle using gas chromatography by removing 250 µL of gas from the 250 mL bottle using a six port, two-position gas sampling valve (Valco #EC6W) interfaced directly to a GC column having FID detector previously calibrated with a 6-point 1-butene (99.0% pure, Scott Specialty Gases, Plumsteadville, Pa.; also known as Air Liquide America Specialty Gases LLC) calibration curve. Employing this method, the yield of complexed 1-butene/c/α-CD was found to be 98%.

Example 2

The 1-butene/c/α-CD from Example 1 was dry sieved using a Micro Sieve set (obtained from Scienceware, Wayne, N.J.; catalog no. F37845-1000) consisting of 4 sections and 4 mesh screens (325, 125, 88 and 60 µm), which separates five particle sizes. Approximately 25 grams of 1-butene/c/α-CD was placed into the top sieve section and the set was place on a wrist-hand shaker (Barnstead Lab-Line model 3589, obtained from Thermo Fisher Scientific of Waltham, Mass.) set at medium speed for 1 hour. The five 1-butene/c/α-CD particle sizes were removed and placed into tared 4 oz. glass jars. The dry sieving process was repeated 5 times. The resulting particle size distribution of 1-butene/c/α-CD is shown in Table 2.

TABLE 2

Particle size distribution of 1-butene/c/α-CD after sieving.

| Particle Size (µm) | Wt % |
|---|---|
| >350 | 15.5% |
| 350-125 | 70.3% |
| 125-88 | 3.1% |
| 88-60 | 8.5% |
| <60 | 2.5% |

Example 3

A full electrostatic printing toner cartridge (Brother TN-420 replacement toner cartridge, obtained from Brother International Corp. of Bridgewater, N.J.) was emptied by removing a large plastic plug filling hole found on the side of the cartridge and collecting the free-flowing toner in a tared 6 oz HDPE plastic bottle. Once the cartridge was empty, the hole was resealed with the plug by twisting it until completely seated. The tared bottle was weighed, then 10 wt % of a 1-butene/c/α-CD complex (unsieved) was added to the toner material based on the weight of the toner. This mixture was shaken for 10 minutes on a wrist-hand shaker (Barnstead Lab-Line model 3589, obtained from Thermo Fisher Scientific of Waltham, Mass.) set at medium speed. Following the mixing process, the toner was returned to the cartridge via the hole from which it was originally emptied. After refilling the cartridge, it was gently shaken side to side to distribute the toner mixture.

The refilled cartridge was mounted in a Brother DCP-7065DN monochrome laser multi-function copier (obtained from the Brother International Corp. of Bridgewater, N.J.) according to the manufacturer's directions. A diamond pattern image representing 35% of total printable area and having a black color (that is, maximum print density) was created using MICROSOFT® Excel software (obtained from MICROSOFT® Corporation of Redmond, Wash.) on a computer connected in electronic communication with the DCP-7065DN printer. The copier was loaded with plain white copy paper, then six (6) paper sheets were printed with the image and discarded. Then three (3) additional sheets were printed from the photo copier and kept for testing. Then the printer was loaded with transparency film (polyester film, 120 microns thick, obtained from the 3M Company of St. Paul, Minn.) and three (3) transparency film sheets were printed and kept for testing.

A paper cutter was used to cut replicate 7.6 cm by 25.4 cm rectangles from each of the three paper sheets and each of the three transparency film sheets. The samples were individually placed in 250 mL glass serum bottles. Then 100 µL of deionized water was injected into each bottle. Care was taken so that the liquid water did not directly contact the sample sheets. The bottles were then sealed with TEFLON® faced silicone rubber septa. Then 1-butene was measured in the headspace at about 17, 43 and 160 hours after the injection of water into the bottle by removing 250 µL of headspace gas using a six port, two-position gas sampling valve (Valco #EC6W, obtained from Valco Instruments Inc. of Houston, Tex.) interfaced directly to a gas chromatograph (GC; Hewlett Packard 5890, obtained from the Hewlett Packard Company of Palo Alto, Calif.) using a RTx-5 GC column, 30 m×0.25 mm I.D., 0.25 µm film (obtained from Restek, Inc., of Bellefonte, Pa.) equipped with a flame ionization detector (FID) and quantitated against a 6-point 1-butene (99.0% pure, Scott Specialty Gases, Plumsteadville, Pa.; also known as Air Liquide America Specialty Gases LLC) calibration curve. Employing this method, the amount of 1-butene released (measured as µL/L-v/v) from the printed sheets containing 1-butene/c/α-CD toner mixture is found in Table 3.

TABLE 3

1-Butene released from electrostatically printed paper and transparency film sheets having a 35% area diamond pattern into the headspace of a 250 mL glass serum bottle.

| Printed Substrate | 17 Hrs µL/L | 43 Hrs µL/L | 160 Hrs µL/L |
|---|---|---|---|
| Paper | 1.04 | 1.23 | 1.26 |
| Paper | 1.03 | 1.21 | 1.30 |
| Paper | 1.06 | 1.19 | 1.26 |
| Film | 1.06 | 1.16 | 1.40 |
| Film | — | 1.21 | 1.26 |
| Film | — | 1.19 | 1.57 |

Example 4

A new electrostatic printing toner cartridge (Brother TN-225Y replacement yellow toner cartridge, obtained from Brother International Corp. of Bridgewater, N.J.) was emptied by cutting a 17 mm filling hole using a tool that melts a ring into the toner cartridge and collecting the free-flowing toner in a tared 6 oz. HDPE plastic bottle. After emptying the cartridge, the hole was resealed. The weight of the toner was determined from the tared bottle. Then 30 grams of TM-toner (yellow) B4C toner (obtained from TM-toner, http://www.tm-toner.com/) was added to a tared 6 oz. HDPE bottle, then 10 wt % of a 1-butene/c/α-CD complex (unsieved) was added to the bottle. The contents of the bottle were shaken for 10 minutes on a wrist-hand shaker (Barnstead Lab-Line model 3589, obtained from Thermo Fisher Scientific of Waltham, Mass.) set at medium speed. Following the mixing process, the toner was returned to the cartridge via the hole from which it was originally emptied, and the cartridge was resealed to form a modified cartridge. The modified cartridge was gently shaken side to side by hand to distribute the toner mixture. The modified cartridge was mounted in a Brother MFC-9340 CDW laser multi-function color copier (obtained from the Brother International Corp. of Bridgewater, N.J.) according to the manufacturer's directions to provide a modified printer.

A solid yellow continuous rectangle image having a total printable area of 20 cm×26.4 cm and having a maximum yellow density was designed on a computer using MICROSOFT® Excel software. The image was then printed onto standard photocopier paper using a HP Laser Jet 5550dn (obtained from the Hewlett-Packard Company of Palo Alto, Calif.). The solid yellow printed paper sheet was placed onto the modified Brother MFC-9340 CDW copier image scanner glass and scanned to the printer memory. The modified printer settings were set to print to "plain paper", and print emulation of "HP LaserJet".

The modified printer was loaded with plain white copy paper (Boise X-9 Copier paper, 20 lb., 8.5"×11", obtained from Packaging Corporation of America of Minneapolis, Minn.), and six (6) paper sheets were printed with the image and discarded. Then three (3) additional sheets were printed from the photo copier and kept for testing. The print weight of toner added to each piece of paper averaged about 550 µg/cm². Then the paper was removed from the modified printer and the modified printer was loaded with polyester film, 8.5"×11" and 120 µm thick, obtained from the 3M Company of St. Paul, Minn.) and three (3) film sheets were printed and kept for testing. The print weight of toner added to the film averaged about 680 µg/cm².

A paper cutter was used to cut replicate 10.2 cm×20.3 cm rectangular samples from the yellow printed areas of each of the three paper sheets and each of the three transparency film sheets. Each individual sample was placed in a 250 mL glass serum bottle sealed with a septum cap. Then 200 µL of deionized water was injected into each bottle. Care was taken so that the liquid water did not directly contact the sample sheets. The bottles were then sealed with TEFLON® faced silicone rubber septa. Then 1-butene was measured in the headspace at about 4, 24 and 96 hours after the injection of water into the bottle by removing 250 µL of headspace gas using a six port, two-position gas sampling valve (Valco #EC6W, obtained from Valco Instruments Inc. of Houston, Tex.) interfaced directly to a gas chromatograph (GC; Hewlett Packard 5890, obtained from the Hewlett Packard Company of Palo Alto, Calif.) using a RTx-5 GC column, 30 m×0.25 mm I.D., 0.25 µm film (obtained from Restek, Inc., of Bellefonte, Pa.) equipped with a flame ionization detector (FID) and quantitated against a 6-point 1-butene (99.0% pure, Scott Specialty Gases, Plumsteadville, Pa.; also known as Air Liquide America Specialty Gases LLC) calibration curve. Employing this method, the amount of 1-butene released (measured as µL/L-v/v) from the printed sheets containing 1-butene/c/α-CD toner mixture is found in Table 4.

TABLE 4

Release of 1-butene from the printed samples of Example 4.

| Printed Substrate | 1-butene, µL/L | | |
|---|---|---|---|
| | 4 Hrs | 24 Hrs | 96 Hrs |
| Paper | 11 | 39 | 70 |
| Paper | 20 | 41 | 51 |
| Paper | 9.9 | 34 | 66 |
| Film | 28 | 74 | 75 |
| Film | 44 | 113 | 115 |
| Film | 25 | 85 | 89 |

Example 5

A miniature pyrometer IR-temperature sensor, model CT-SF22-C1 (obtained from Micro-Epsilon Messtechnik GmbH & Co. of Ortenburg, Germany) was used to measure the fuser temperature of the Brother MFC-9340 CDW during printing. The IR sensor (8 to 14 µm range) has a 7 mm diameter surface measurement at an optical focus from 0-100 mm. The IR sensor was installed inside the photo copier permitting fuser temperature measurements directly on the fuser surface unobstructed by the movement of paper through the copier during printing. This permitted measuring fuser temperature when using different paper tray setting (thin, plain paper, thick, thicker and recycled paper) and print emulations (HP LaserJet and BR Script-3).

Example 6

A new electrostatic printing toner cartridge (Brother TN-225Y replacement yellow toner cartridge, obtained from Brother International Corp. of Bridgewater, N.J.) was emptied into a tared 6 oz. HDPE plastic bottle, then resealed employing the procedure of Example 4. Then 35 grams of X-GENERATION® yellow toner no. 18532 (yellow replacement toner obtained from 123Toner, http://www.123toner.com) was added to a 6.5 oz. PET beaker, then 2.8 wt % of the 1-butene/c/α-CD complex of Example 2, sieved fraction <60 µm was slowly added to the contents of the beaker while mixing. Then the contents of the beaker were mixed for one (1) hour using the technique described in U.S. Pat. No. 6,599,673 using a mixing blade similar to FIG. 5. Following the mixing/blending process, the toner was returned to the cartridge via the hole from which the contents were originally emptied. After refilling the cartridge, it was gently shaken side to side to distribute the toner mixture.

The refilled cartridge was mounted in a Brother MFC-9340 CDW laser multi-function color copier (obtained from the Brother International Corp. of Bridgewater, N.J.) according to the manufacturer's directions. The solid yellow continuous printed image of Example 4 was employed for print testing; this pattern is referred to below as "100%". A second image consisting of a maximum yellow density diamond pattern having overall dimensions of 20 cm×26.4 cm but representing 50% of total yellow area of the image of Example 4 was designed on a computer using MICROSOFT® Excel software; this image is referred to below as "50%".

Both the 100% and the 50% images were printed onto separate sheets of photocopier paper using a HP Laser Jet 5550dn (obtained from the Hewlett-Packard Company of Palo Alto, Calif.). The 100% printed paper was placed onto the Brother MFC-9340 CDW copier image scanner glass. The laser printer settings were set to the same settings as for Example 4. The image was scanned to the copier.

The copier was loaded with plain white copy paper as used in Example 4. Then six (6) paper sheets were printed with the scanned image and discarded. Then two (2) additional sheets were printed with the same scanned image and kept for testing. The average toner print weight per tested print was about 160 μg/cm². Then the printer was loaded with PET film (8.5"×11"×110 μm thick, obtained from the ACCO Brands of Zurich, Ill.) and two (2) transparency film sheets were printed using the same scanned image, and kept for testing. The average toner print weight per tested printed film was about 80 μg/cm². Fuser temperature measurements were acquired during printing; these are shown in Table 5.

A paper cutter was used to cut replicate 7.6 cm by 20.3 cm rectangles from the printed areas of each of the two paper sheets and each of the two transparency film sheets. The samples were individually placed in 250 mL glass serum bottles. Then 200 μL of deionized water was injected into each bottle. Care was taken so that the liquid water did not directly contact the sample sheets. The bottles were then sealed with TEFLON® faced silicone rubber septa. Then 1-butene was measured in the headspace at about 4, 24 and 96 hours after the injection of water into the bottle by removing 250 μL of headspace gas using a six port, two-position gas sampling valve (Valco #EC6W, obtained from Valco Instruments Inc. of Houston, Tex.) interfaced directly to a gas chromatograph (GC; Hewlett Packard 5890, obtained from the Hewlett Packard Company of Palo Alto, Calif.) using a RTx-5 GC column, 30 m×0.25 mm I.D., 0.25 μm film (obtained from Restek, Inc., of Bellefonte, Pa.) equipped with a flame ionization detector (FID) and quantitated against a 6-point 1-butene (99.0% pure, Scott Specialty Gases, Plumsteadville, Pa.; also known as Air Liquide America Specialty Gases LLC) calibration curve. Employing this method, the amount of 1-butene released (measured as μL/L-v/v) from the printed sheets containing 1-butene/c/α-CD toner mixture is reported in Table 5.

Next, the 50% printed paper was placed onto the Brother MFC-9340 CDW copier image scanner glass and the scanning, printing, cutting, and headspace analysis procedures employed for the 100% image were repeated using the 50% image. The results are reported in Table 5.

TABLE 5

Fuser temperatures during printing, and release of 1-butene from the Brother MFC-9340 CDW printed samples of Example 6.

| Printed Substrate | Paper Setting | Fuser Temp, ° C. | % Print Coverage | 1-butene, μL/L | | | | |
|---|---|---|---|---|---|---|---|---|
| | | | | 1 Hr | 2 Hrs | 4 Hrs | 8 Hrs | 24 Hrs |
| Paper | Thick | 170 | 100 | 0.04 | 0.06 | 0.10 | 0.13 | 0.28 |
| Paper | Thick | 170 | 100 | 0.04 | 0.06 | 0.09 | 0.06 | — |
| Paper | Thin | 160 | 100 | 0.07 | 0.09 | 0.14 | 0.23 | 0.51 |
| Paper | Thin | 165 | 100 | 0.04 | 0.07 | 0.12 | 0.25 | 0.55 |
| Paper | Thin | 165 | 50 | ND | 0.05 | 0.01 | 0.02 | 0.04 |
| Paper | Thin | 165 | 50 | 0.05 | 0.07 | 0.11 | 0.15 | 0.55 |
| Film | Thick | 170 | 100 | 0.06 | 0.26 | 0.48 | 0.10 | 1.5 |
| Film | Thick | 170 | 100 | 0.30 | 0.59 | 0.98 | 1.4 | 1.9 |
| Film | Thin | 165 | 100 | 0.13 | 0.60 | 1.17 | 1.5 | — |
| Film | Thin | 165 | 100 | 0.44 | 0.81 | 1.33 | 2.2 | 2.4 |
| Film | Thin | 165 | 50 | 0.09 | 0.18 | 0.36 | 0.60 | 0.78 |
| Film | Thin | 165 | 50 | 0.10 | 0.25 | 0.48 | 0.72 | 0.90 |

Example 7

To 1.5 grams of the 1-butene/c/α-CD complex of Example 2 (sieved fraction <60 μm) was added with 0.125 wt % 2,5-dihydroxybenzoic acid (2,5-DHB). The 2,5-DHB was ground using a mortar and pestle and then passed through a 45 μm sieve before adding to 1-butene/c/α-CD complex. The mixture was placed into a 20 mL glass scintillator and rotated on a Spiramix 5 (obtained from Ortho Diagnostic Systems GmbH, Neckargemünd, Germany) for 2 hours.

Example 8

A new electrostatic printing toner cartridge (Brother TN-225Y replacement yellow toner cartridge, obtained from Brother International Corp. of Bridgewater, N.J.) was emptied into a tared 6 oz. HDPE plastic bottle, then resealed employing the procedure of Example 4. Then 25 grams of X-Generation® yellow toner no. 18532 (yellow replacement toner obtained from 123Toner.com) was added to a 6.5 oz. PET beaker, then 2.8 wt % of the 1-butene/c/α-CD complex of Example 2 was added to the yellow toner material slowly while mixing. This mixture was mixed for one (1) hour using the procedure of Example 6. Following the mixing/blending process, the toner was returned to the cartridge via the hole from which it was originally emptied. After refilling the cartridge, it was gently shaken side to side to distribute the toner mixture.

The refilled cartridge was mounted in a Brother MFC-9340 CDW laser multi-function color copier (obtained from the Brother International Corp. of Bridgewater, N.J.) according to the manufacturer's directions. The 100% and 50% (diamond) images of Example 6 were used, and printed onto photocopier paper using a HP Laser Jet 5550dn.

The 100% printed paper was placed onto the Brother MFC-9340 CDW copier image scanner glass. The image was scanned using settings as for Example 6. The copier was loaded with plain white copy paper (Boise copier paper, 20 lb.), and then six (6) paper sheets were printed with the scanned image and discarded. Then two (2) additional sheets were printed and kept for testing. The average toner print weight per piece of printed test paper was 160 µg/cm². Then the printer was loaded with polyester film (8.5"×11"×110 µm thick, obtained from the ACCO Brands of Zurich, Ill.) and two (2) film sheets were printed and kept for testing. The average toner print weight per piece of test film was 80 µg/cm². Fuser temperature measurements were acquired during printing; these are shown in Table 6.

A paper cutter was used to cut replicate 7.6 cm by 20.3 cm rectangles from each of the two paper sheets and each of the two transparency film sheets. The samples were individually placed in 250 mL glass serum bottles. Then 200 µL of deionized water was injected into each bottle. Care was taken so that the liquid water did not directly contact the sample sheets. The bottles were then sealed with TEFLON® faced silicone rubber septa. Then 1-butene was measured in the headspace at about 4, 24 and 96 hours after the injection of water into the bottle by removing 250 µL of headspace gas using a six port, two-position gas sampling valve (Valco #EC6W, obtained from Valco Instruments Inc. of Houston, Tex.) interfaced directly to a gas chromatograph (GC; Hewlett Packard 5890, obtained from the Hewlett Packard Company of Palo Alto, Calif.) using a RTx-5 GC column, 30 m×0.25 mm I.D., 0.25 µm film (obtained from Restek, Inc., of Bellefonte, Pa.) equipped with a flame ionization detector (FID) and quantitated against a 6-point 1-butene (99.0% pure, Scott Specialty Gases, Plumsteadville, Pa.; also known as Air Liquide America Specialty Gases LLC) calibration curve. Employing this method, the amount of 1-butene released (measured as µL/L-v/v) from the printed sheets containing 1-butene/c/α-CD toner mixture is found in Table 6.

Next, the 50% printed paper was placed onto the Brother MFC-9340 CDW copier image scanner glass and the scanning, printing, cutting, and headspace analysis procedures employed for the 100% image were repeated using the 50% image. The results are reported in Table 6.

The invention illustratively disclosed herein can be suitably practiced in the absence of any element which is not specifically disclosed herein. While the invention is susceptible to various modifications and alternative forms, specifics thereof have been shown by way of examples, and are described in detail. It should be understood, however, that the invention is not limited to the particular embodiments described. On the contrary, the intention is to cover modifications, equivalents, and alternatives falling within the spirit and scope of the invention. In various embodiments, the invention suitably comprises, consists essentially of, or consists of the elements described herein and claimed according to the claims.

Additionally each and every embodiment of the invention, as described here, is intended to be used either alone or in combination with any other embodiment described herein as well as modifications, equivalents, and alternatives thereof falling within the spirit and scope of the invention. The various embodiments described above are provided by way of illustration only and should not be construed to limit the claims attached hereto. It will be recognized that various modifications and changes may be made without following the example embodiments and applications illustrated and described herein, and without departing from the true spirit and scope of the claims.

The invention claimed is:

1. A printed substrate comprising a substrate having a first major surface, the printed substrate comprising a first electrostatically printable composition electrostatically printed and at least partially fused on at least a portion of the area of the first major surface, the first electrostatically printable composition comprising a particulate comprising a cyclodextrin complexed with a first medicament, further wherein the cyclodextrin is present in the printable composition at about 2 wt % to 30 wt %.

2. The printed substrate of claim 1 wherein the substrate comprises a nonwoven or a solid polymeric sheet.

3. The printed substrate of claim 1 wherein the first electrostatically printable composition further comprises a colorant.

4. The printed substrate of claim 1 further comprising a second electrostatically printable composition electrostatically printed on at least a portion of the area of the first major surface, the second electrostatically printable composition comprising a particulate comprising a cyclodextrin complexed with a second medicament, wherein the second medicament is different from the first medicament.

5. The printed substrate of claim 4 wherein the second electrostatically printable composition further comprises a colorant.

6. The printed substrate of claim 4 wherein one of the first or second medicaments is an anti-inflammatory or an antibiotic.

7. The printed substrate of claim 1 further comprising a laminating substrate contacting the first major surface.

8. The printed substrate of claim 1 further comprising a water activated adhesive disposed on the first major surface.

TABLE 6

Fuser temperatures during printing, and release of 1-butene from the printed samples of Example 8.

| Printed Substrate | Paper Setting | Fuser Temp, ° C. | % Print Coverage | 1 Hr µL/L | 2 Hrs µL/L | 4 Hrs µL/L | 8 Hrs µL/L | 24 Hrs µL/L |
|---|---|---|---|---|---|---|---|---|
| Paper | Thin | 170 | 100 | 0.14 | 0.19 | 0.29 | 0.49 | 1.0 |
| Paper | Thin | 170 | 100 | 0.12 | 0.19 | 0.29 | 0.49 | 1.9 |
| Paper | Thin | 165 | 50 | 0.04 | 0.07 | 0.12 | 0.19 | 0.33 |
| Paper | Thin | 165 | 50 | 0.06 | 0.08 | 0.12 | 0.19 | 0.33 |
| Film | Thin | 175 | 100 | 0.10 | 0.71 | 0.58 | 0.99 | 1.5 |
| Film | Thin | 175 | 100 | 0.43 | 0.67 | 1.1 | 1.8 | 2.4 |
| Film | Thin | 165 | 50 | 0.09 | 0.18 | 0.36 | 0.56 | 0.78 |
| Film | Thin | 165 | 50 | 0.10 | 0.25 | 0.48 | 0.72 | 0.90 |

9. The printed substrate of claim 8 wherein water triggers the release of the first medicament from the cyclodextrin complex thereof.

10. The printed substrate of claim 1 further comprising an adhesive disposed on a second major surface of the substrate.

11. The printed substrate of claim 10 further comprising a liner contacting the adhesive.

12. The printed substrate of claim 1 wherein the substrate is a water soluble or saliva soluble film.

13. The printed substrate of claim 12 wherein water triggers the release of the first medicament from the cyclodextrin complex.

14. A printed substrate comprising:

a substrate having a first major surface and a second major surface; and a first electrostatically printable composition electrostatically printed on at least a portion of the first major surface and at least partially fused thereon, the first electrostatically printable composition comprising a particulate comprising cyclodextrin complexed with a first compound selected from an antimicrobial, a fungicide, an insecticide, a pesticide, a preservative, or a fragrance, further wherein the cyclodextrin is present in the printable composition at about 2 wt % to 30 wt %; and an adhesive disposed on at least a portion of the second major surface of the substrate.

15. The printed substrate of claim 14 wherein the first electrostatically printable composition further comprises a colorant.

16. The printed substrate of claim 14 further comprising a laminating substrate contacting the first major surface.

17. The printed substrate of claim 14 further comprising a second electrostatically printable composition electrostatically printed on at least a portion of the area of the first major surface, the second electrostatically printable composition comprising a particulate comprising cyclodextrin complexed with a second compound selected from an antimicrobial, a fungicide, an insecticide, a pesticide, a preservative, or a fragrance, wherein the second compound is different from the first compound.

18. The printed substrate of claim 17 wherein the second electrostatically printable composition further comprises a colorant.

19. A kit comprising a plurality of die-cut stickers, the stickers comprising the printed substrate of claim 14.

* * * * *